(12) United States Patent
Klimyuk et al.

(10) Patent No.: US 8,003,381 B2
(45) Date of Patent: Aug. 23, 2011

(54) AMPLIFICATION VECTORS BASED ON TRANS-SPLICING

(75) Inventors: Victor Klimyuk, Halle/Saale (DE); Peter Ivanov, Moscow (RU); Sylvestre Marillonnet, Halle/Saale (DE); Meinhart Zenk, Halle/Saale (DE); Yuri Gleba, Halle/Saale (DE)

(73) Assignee: Icon Genetics GmbH, Munich (DE)

( * ) Notice: Subject to any disclaimer, the term of this patent is extended or adjusted under 35 U.S.C. 154(b) by 0 days.

(21) Appl. No.: 10/512,920

(22) PCT Filed: Apr. 30, 2002

(86) PCT No.: PCT/EP02/04764
§ 371 (c)(1),
(2), (4) Date: Oct. 29, 2004

(87) PCT Pub. No.: WO02/097080
PCT Pub. Date: Dec. 5, 2002

(65) Prior Publication Data
US 2005/0221323 A1 Oct. 6, 2005

(51) Int. Cl.
*C12N 15/00* (2006.01)
*C12N 15/82* (2006.01)
*C07H 21/04* (2006.01)

(52) U.S. Cl. .......... 435/320.1; 536/23.72; 800/278
(58) Field of Classification Search .......... None
See application file for complete search history.

(56) References Cited

U.S. PATENT DOCUMENTS

| 5,869,254 A | 2/1999 | Sullenger et al. |
| 6,071,730 A | 6/2000 | Haseloff et al. |
| 6,632,980 B1 * | 10/2003 | Yadav et al. .......... 800/278 |

FOREIGN PATENT DOCUMENTS

| WO | WO 92/13090 | 8/1992 |
| WO | WO 00/17342 | * 3/2000 |
| WO | WO 02/29068 | 4/2002 |

OTHER PUBLICATIONS

Thomas et al. 2001, The Plant Journal 25(4):417-425.*

* cited by examiner

*Primary Examiner* — Li Zheng
(74) *Attorney, Agent, or Firm* — Alston & Bird LLP

(57) ABSTRACT

This invention provides a process of amplification and/or expression of a sequence of interest in a cell by providing for generating within the cell at least one amplicon by trans-splicing between an RNA sequence designed for being capable of trans-splicing and a target RNA, whereby the amplicon is capable of amplifying in the cell and capable of expressing a sequence of interest.

32 Claims, 14 Drawing Sheets

AMPLIFICATION VECTORS BASED ON TRANS-SPLICING

FIELD OF THE INVENTION

The present invention relates to a process of expressing a sequence of interest in a cell, notably in a plant cell. The invention further related to a method of increasing the efficiency of trans-splicing.

BACKGROUND OF THE INVENTION

One of the early applications of the trans-splicing phenomenon has been proposed by Sullenger and Cech (*Nature*, 1994, 371, 619-622) who described experiments in which ribozyme-mediated trans-splicing was used to replace a defective portion of RNA with a functional structure by using reengineered Tetrahymena group I intron to generate translatable lacZ transcripts in *E. coli*. They proposed trans-splicing as a general means of altering the sequence of specific host transcripts for the purposes of treatment of many genetic diseases. Another use of trans-splicing has been proposed by Ayre and colleagues, (1999, *Proc. Natl. Acad. Sci. USA*, 96, 3507-3512,), who developed a technology that utilizes ribozyme-mediated trans-splicing to target cytotoxins into cells in a highly specific manner. They used group I intron to splice the mRNA for Diphteria toxin A with virus mRNA to inactivate cells expressing viral mRNA, thus selectively inactivating infected yeast cells.

Yet another important application has been developed by Mikheeva and Jarrell (1996, *Proc. Natl. Acad. Sci. USA*, 93, 7486-7490) who used engineered group II introns to catalyze assembly of a chimeric gene. In this work, the ribozyme was modified so as to shuffle the mRNA of tissue plasminogen activator, and the resulting chimeric RNA was reverse transcribed into DNA. This approach allows to unidirectionally create libraries of genes that encode chimeric proteins with novel functions.

A general problem encountered in all of the above mentioned approaches is that cleaving ribozymes are unable to deplete living cells of the chosen target RNA. Further, the trans-splicing efficiency is very low leading to very low amounts of trans-spliced RNA in a cell. In many cells, no trans-spliced RNA product is obtained at all. Attempts have been made to use ribozymes with an extended complementarity to the target RNA and to design a precise alteration of the guide sequences required for substrate recognition (Kohler et al., 1999, *J. Mol. Biol.*, 285, 1935-1950). Still, trans-splicing is inefficient and thus the applications of in vivo ribozyme-mediated trans-splicing today are limited to specific inactivation of cells using potent toxins trans-spliced with a highly abundant target RNA (of viral coat protein), a process that can effectively function even in the presence of unspliced target mRNA in a host cell.

It is therefore an object of the invention to provide an efficient process of amplification or expression of a sequence of interest in a cell.

It is an object of the invention to provide a biologically safe process of amplification or expression of a sequence of interest in a cell.

It is another object of the invention to provide an efficient process of assembling RNA, notably mRNA, of interest in a cell from precursor RNA molecules.

It is a further object to provide a process of assembling mRNA in a cell from a residential RNA and an externally provided RNA, whereby the effect of any remaining residential RNA is negligible compared to the assembled RNA.

It is a further object to provide a process of amplifying or down-regulating selected mRNA in a cell.

It is a further object to provide a method of increasing the efficiency of trans-splicing.

GENERAL DESCRIPTION OF THE INVENTION

The above objects are achieved by a process of amplification and/or expression of a sequence of interest in a cell by providing for generating within said cell at least one amplicon, whereby said amplicon is generated by trans-splicing between an RNA sequence designed for being capable of trans-splicing and a target RNA, whereby said amplicon is capable of amplifying in said cell. Preferably, said amplicon is further capable of expressing said sequence of interest.

The inventors have surprisingly found that the above process solves many shortcomings of conventional trans-splicing processes and makes trans-splicing a highly versatile tool in biotechnology. Most importantly, the process of this invention is environmentally safer than processes previously known. Herein, trans-splicing generates an amplicon capable of amplifying in said cells, thus amplifying the product of the trans-splicing event and any sequence of interest present on said amplicon. Said sequence of interest may be expressed from said amplicon.

Providing for generating within said cell at least one amplicon by trans-splicing comprises providing said cell with said RNA sequence designed for being capable of trans-splicing (e.g. a ribozyme). Said cell may be provided with said RNA sequence by any known method. Said RNA sequence may be provided indirectly to said cell by directly providing a DNA sequence capable of being transcribed in said cell to produce said RNA sequence.

Said RNA sequence designed for being capable of trans-splicing preferably contains an intron capable of trans-splicing. An intron capable of trans-splicing may be a self-splicing intron, e.g. a group I or a group II intron. Alternatively, said intron may be an intron of a nuclear pre-mRNA for spliceosome-mediated splicing. Further, it may be a genetically altered or an artificial intron or a pro-intron which upon processing (e.g. by cis-splicing) by the host cell generates an intron or a ribozyme capable of trans-splicing. Self-splicing introns are preferred; group I introns are most preferred. Further, said RNA sequence comprises at least one, preferably at least two sequences complementary to said target RNA. For details on such RNA sequences and ribozymes see below.

Said trans-splicing assembles said amplicon by linking the 5' and the 3' part of said amplicon to be assembled. The 5' part of said amplicon to be assembled may be provided by said RNA sequence or by said target RNA. The 3' part of said amplicon to be assembled may be provided by said target RNA or by said RNA sequence. It is preferred and technically easier to accomplish that said 5' part of the amplicon is provided by said target RNA and said 3' part is provided by said RNA sequence.

Said RNA sequence preferably further comprises other sequences like a sequence of interest. Said sequence of interest may be a sequence to be expressed or a part of a sequence to be expressed. The sequence to be expressed preferably codes for a polypeptide. In this case, the sequence of interest preferably further contains regulatory sequences for enabling translation.

Said sequence of interest may further comprise or code for an RNA sequence that is not intended for translation. It may e.g. comprise sequence portions having self-complementarity for forming a double-stranded structure on the RNA level.

The double-stranded RNA structure may have a portion of sequence identity to a gene of the host cell and may be of sufficient length to inhibit expression of said gene in said cell. This method may be used for down-regulation or silencing of a selected gene of the host cell and for functional genomics studies. The method of genetic inhibition by double-stranded RNA is generally described in WO 99/32619. An efficient method of down-regulating any desired target gene using small interfering RNAs is described in Brummelkamp et al. (Science 296 (2002), 550-553).

Said amplicon comprises an origin of replication for enabling amplification of said amplicon. Said origin of replication may be provided by said RNA sequence. Said origin of replication may also be provided by said target RNA. Alternatively, said RNA sequence and said target RNA may each provide a part of an origin of replication. A functional origin of replication may then be assembled in said trans-splicing reaction.

Said trans-splicing takes place between said RNA sequence designed for being capable of trans-splicing and a target RNA. In a first general embodiment, said target RNA is an RNA native to the host cell (residential RNA). Preferably, said target RNA is an mRNA. This allows to couple a residential RNA to a sequence of interest present on said RNA sequence (e.g. on said ribozyme), e.g. for amplifying or silencing said residential RNA or for expressing a protein encoded by said residential RNA and/or a sequence of interest on said RNA sequence. If said target RNA is an RNA native to said host cell, the origin of replication is preferably provided by said RNA sequence. Said native or residential RNA may of course be derived from a transgene artificially introduced into a precursor cell of said host cell.

In a second general embodiment, said target RNA is introduced into said cell externally. In this embodiment, both parts of said amplicon to be assembled by trans-splicing may be heterologous to said cell. Both parts of said amplicon may be genetically modified as desired, which makes this embodiment particularly flexible. Said target RNA may be introduced into a cell by the same or by a different transformation or transfection method as used for said RNA sequence. Notably, said target RNA and said RNA sequence may be introduced at the same time, e.g. by infecting said cell with a mixture of *Agrobacterium* strains, one carrying said target RNA and one carrying said RNA sequence in the T-DNA on a Ti-plasmid. Another preferred methodology is to first introduce said target RNA via *Agrobacterium* and to provide said RNA sequence at a desired later point in time by way of viral infection. However, there are numerous further possibilities to adjust the steps of this general embodiment to the needs of a particular case.

In said second general embodiment, said target RNA may comprise a sequence of interest similar to said sequence of interest that may be comprised by said RNA sequence. In an important embodiment, assembly of said amplicon by trans-splicing may be used to assemble a sequence of interest from parts thereof, whereby said target RNA and said RNA sequence each provide a part of said sequence of interest. Providing the second part of said sequence of interest either by said target RNA or said RNA sequence may function as a switch to assemble said sequence of interest (e.g. a gene) in a functional form, thus switching on a function or trait conferred to said cell by said assembled sequence of interest. Preferably, the sequence of interest is split and divided such on said RNA sequence and said target RNA that each part, when expressed, is not capable of exerting the function of the sequence of interest. Said sequence of interest may be an antibiotic resistance gene or any other gene conferring a useful trait. An important advantage of this embodiment is that a transgenic plant containing only a part of a functional transgene cannot transfer a functional transgene to cross-progeny or to other organisms, making this technique environmentally safer than prior art processes.

Further, the process of the invention, notably said trans-splicing and/or said amplification, may be used to switch on a biochemical process or biochemical cascade of interest as described in the international patent application PCT/EP02/02091.

If said target RNA is provided externally to said cells, this may be done by viral transfection, *Agrobacterium*-mediated delivery, non-biological delivery, or by conversion of a precursor DNA that was pre-integrated into a nuclear DNA or was maintained in the nucleus autonomously to form the target RNA of the invention.

The process of the invention may be performed on a plant cell or on an animal cell. Plant cells are preferred. Said process may be performed with cells in cell culture. Preferably, said cell may belong to a plant or animal organism. Most preferably, said process is carried out with plants. Said cell may be a wild-type cell or it may be a genetically engineered cell. Said cell may be stably genetically engineered by having introduced a desired sequence into the nuclear or an organelle genome. Further, said cell may be transiently modified. Said genetic engineering may provide said cell with a function necessary for generating an amplicon by trans-splicing. Further, said genetic engineering may provide said cell with a function necessary for amplifying said amplicon, e.g. an RNR-dependent RNA polymerase (RNR/RNR polymerase), a retro transcriptase or a DNA-dependent DNA polymerase. Moreover, said genetic engineering may provide said cell with said target RNA.

Said cell may further be genetically engineered or transiently modified to provide in trans one or more functions necessary for amplification, infectivity, virus particle assembly, suppression of gene silencing, changing the metabolic profile of the cell, reverse transcription, integration into a host chromosome, cell-to-cell or long-distance movement of said resultant amplicon(s), or a functions that is necessary for generating said amplicon by trans-splicing.

In a particularly preferred embodiment, the process of the invention, notably said trans-splicing or amplification of said amplicon, is strictly dependent on said genetical engineering or said transient modification of said cell or of an organism(s) containing said cell(s), thus providing for improved control over said process and/or for improved environmental safety of said process. Further, said amplification may be temporary and may occur exclusively during a period of time during which one or more functions necessary for said amplification is provided transiently. This may e.g be achieved by providing an RNA/RNA polymerase transiently. Removal of selection pressure may lead to loss of a vector encoding said polymerase. For example, said temporary amplification may be controlled by factors provided transiently through *Agrobacterium*.

The direct product of said trans-splicing is an RNA molecule. In an important embodiment, said direct product of trans-splicing is said amplicon of the invention. Alternatively, the amplicon of the invention may be a DNA amplicon. In this case, the RNA molecule directly produced by said trans-splicing will have to be reverse transcribed to produce said DNA amplicon. Unless said cell already contains the gene of an RNA-dependent DNA polymerase (reverse transcriptase) e.g. from a retro transposon, said cell may have to be provided with such a reverse transcriptase. The DNA amplicon may be related to a DNA virus or may be of DNA virus origin. It is however preferred, that said RNA molecule produced by trans-splicing is an amplicon, i.e. an RNA amplicon.

Further, said amplicon may be of retroviral or of retrotransposon origin or may have selected properties of a retrovirus or a retrotransposon. Said properties of retroviral or retrotransposon origin allow for example to incorporate a sequence of interest into the nuclear genome of the host cell.

If said amplicon is an RNA amplicon, the RNA amplicon may be related to an RNA virus or it may be of RNA virus origin. This means for example, that said origin of replication is preferably the origin of replication of said RNA virus. The RNA amplicon may encode the RNA-dependent RNA polymerase of said RNA virus that can recognize the origin of replication of the amplicon. Since the process of the invention is preferably carried out on plant cells, said RNA virus is preferably a plant virus. Preferred plant viruses are those belonging to the tobamoviridae, e.g. tobacco mosaic virus.

Said cell may be provided with said RNA sequence by viral transfection, *Agrobacterium*-mediated delivery, non-biological delivery, or by conversion of a precursor DNA that was pre-integrated into a nuclear DNA or was maintained in the nucleus autonomously to form an RNA sequence designed for being capable of trans-splicing with a target RNA. Non-biological delivery includes particle bombardment, PEG-mediated transformation of plant protoplast, and electroporation. For *Agrobacterium* and non-biological delivery, the cell is preferably provided with DNA capable of being transcribed in said cell to form said RNA sequence. Viral transfection may be done with RNA or with DNA.

Said cell may be provided with two or more RNA sequences by the same or by different methods. Said two or more RNA sequences may be provided simultaneously (in a one-step process) or consecutively (in a two-step process). Thereby, said trans-splicing may produce two or more types of amplicons.

One of said amplicons may be a fully functional autonomous amplicon that is capable of amplification in said cell and that provides in trans functions necessary for replication of other non-autonomous amplicon(s). Further, one of said amplicons may be essentially a wild type virus or an attenuated wild type virus which provides in trans one or more functions necessary for replication of other amplicon(s). Moreover, one or more of said amplicons may retain other viral or retrotransposon functions such as infectivity, ability to assemble viral particles, cell to cell movement, reverse transcription, integration into a host chromosome or systemic movement.

The processes of the invention are performed with multi-cellular plant or animal organisms. Multi-cellular plants are preferred. Among animals, mammals (e.g. mice, rats, rabbits, and animals used for human nutrition like pigs and bovine animals) are preferred. Humans are excluded. Among plants, crop plants including barley, oat, rye, wheat, *zea mays*, rice, millet, potato, oilseed rape, canola, and tobacco are preferred.

The process of the invention may be used for a wide variety of applications. It may e.g. be used for expressing a sequence of interest. Further, it may be used for amplifying or expressing more than one sequence of interest, e.g. sequences of interest necessary for simultaneous production of polypeptides required e.g. for multimer protein production. A preferred example of said protein multimer is an immune response protein such as human or animal monoclonal antibody. Moreover, said process may result in amplification and/or expression of at least two genes of a biochemical pathway or cascade, whereby a whole biochemical pathway may be introduced in a cell or an organism.

Further, the process of the invention may result in amplification and/or expression of sequences of interest for the purpose of functional genomics, gene identification, gene function determination, biochemical pathway analysis and/or for selective screening. Further, said trans-splicing may assemble an RNA sequence of interest or a transcription unit, whereby said RNA sequence and said target RNA each provide a part of said sequence of interest or of said transcription unit. In said transcription unit, genetic elements selected from the following group may be assembled: transcriptional and translational signals or elements; introns, exons, inteins or exteins; signal, transit, targeting or attachment motifs; purification and visualization tags; catalytic, recognition, affinity or other functional domains or parts thereof, whereby said genetic elements are derived from one or more genes or are engineered artificially.

The process of the invention may further be used for specific amplification and/or expression of nucleic acid sequences for the purpose of biochemical production or therapy.

The invention also allows to assemble a sequence coding for a protein with modules of e.g. signal peptides, binding domains, retention signals, compartmentalisation signals, activation domains, domains with enzymatic activities, affinity tags, and regulatory sequences. Such a modular approach makes allows to find an optimal expression cassette for a specific purpose or for finding an optimal secretory or transit peptide for a specific gene to be overexpressed and accumulated in the cell or a specific compartment thereof. It can be a valuable tool for functional genomics and proteomics studies. A library of plants may e.g. be created, whereby each member of the library contains a particular module (e.g. a specific signal peptide) of one of the above module classes e.g. as said target RNA. Said RNA sequence may then code for a protein of interest to be linked e.g. to a signal peptide.

Preferred embodiments of the invention are as follows:

A process of amplification and/or expression of a sequence of interest in a cell by providing said cell with an RNA sequence designed for being capable of trans-splicing with a target RNA, and providing said cell with said target RNA that is specifically recognized by said RNA sequence, thus generating within said cell at least one amplicon resulting from said trans-splicing between said RNA sequence and said target RNA, whereby said amplicon is capable of amplifying in said cell and capable of expressing a sequence of interest.

A process of amplification and/or expression of a sequence of interest in a plant cell by providing for generating within said plant cell at least one amplicon by trans-splicing between an RNA sequence designed for being capable of trans-splicing and a target RNA, whereby said amplicon is capable of amplifying in said plant cell and capable of expressing a sequence of interest, whereby said plant cell is provided with said RNA sequence by providing said cell with a DNA sequence capable of being transcribed in said cell to produce said RNA sequence, and whereby said target RNA is an RNA transcript of a gene native to said plant cell.

A process of amplification and/or expression of a sequence of interest in a plant cell by providing for generating within said plant cell at least one amplicon by trans-splicing between an RNA sequence designed for being capable of trans-splicing and a target RNA, whereby said amplicon is capable of amplifying in said cell and capable of expressing a sequence of interest; whereby said plant cell is provided with said RNA sequence by providing said plant cell with a DNA sequence capable of being transcribed in said cell to produce said RNA sequence, and whereby said target RNA is provided to said plant cell by transformation or transfection.

In the above preferred embodiments, the 5' end of said amplicon is preferably provided by said target RNA and the 3' end of said amplicon is provided by said RNA sequence.

The invention further provides cells, tissues, organism or material thereof obtained or obtainable by performing the process of the invention. Further, vectors or pro-vectors are provided for performing the process of the invention. Said vector preferably has or codes for an RNA sequence capable of trans-splicing with a target RNA. Further, said RNA sequence of said vector preferably contains a sequence functional as an origin of replication, most preferably on the RNA level (e.g. plant RNA viral origin of replication). Moreover, a kit-of-parts comprising (i) plant cells, plant seeds, plants or animal cells or animals and (ii) said vectors or precursors thereof. Said vectors may be contained in *Agrobacteria*.

DETAILED DESCRIPTION OF THE INVENTION

Figure 1:
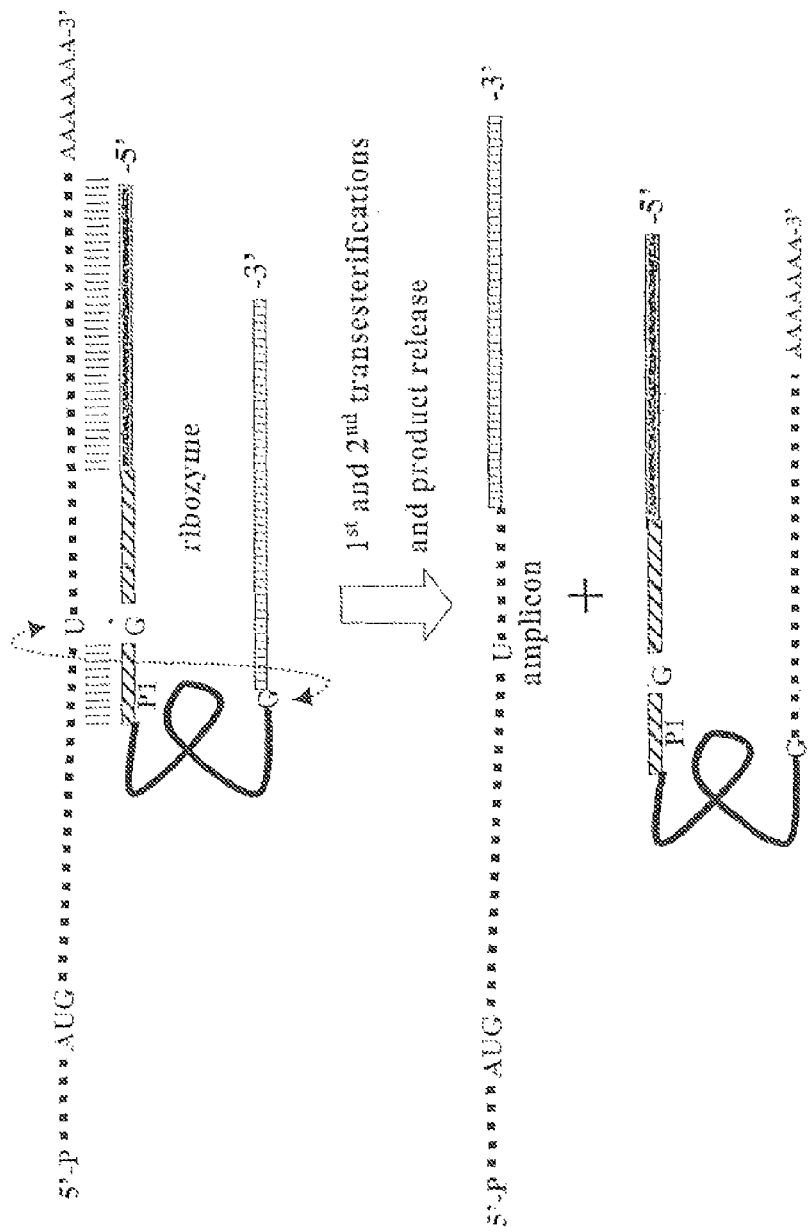
FIG. 1 General scheme of trans-splicing resulting in amplicon formation.

To circumvent the inefficiency of the technologies based on RNA trans-splicing, we have developed a system in which trans-splicing generates molecules that are capable of amplification, thus the end result of the process is an amplicon or a number of amplicons that allows to amplify both the nucleic acid(s) of interest, as well as the products of expression thereof. To the best of our knowledge, there is no prior art describing such a solution. By using the process of the invention, the ratio of spliced versus unspliced mRNAs in a host cell can be dramatically changed in favor of the spliced product. The approach requires the simultaneous presence in a host cell of all precursor components necessary for assembly of amplicons, which process was triggered as a result of a specific trans-splicing. The general scheme of such trans-splicing leading to the formation of amplicons from amplicon elements or pro-amplicons is shown in FIG. 1. The interaction between two pro-amplicon RNA molecules, triggered by the engineered ribozyme, assembles functional RNA molecules capable of amplification.

The trans-splicing reaction is not limited to the use of group I introns and their derivatives. There are different groups/classes of introns classified according to their internal organization and mechanism of splicing. Nuclear introns have in common the possession of GT-AG dinucleotides at the 5' and 3' ends and usually require spliceosome formation for their splicing. Group I and group II introns were named after introns found in different fungal mitochondrial genes. They are classified according to their internal organization but have in common the ability to autocatalyze their own splicing.

Nuclear introns are spliced through a snRNP-mediated (spliceosome-mediated) mechanism. There is abundant literature describing the mechanisms of cis-splicing including alternative splicing of nuclear genes in different eukaryotic organisms (for review see Adams et al., 1996, *Curr. Opin. Cell Biol.*, 8, 331-339; Hastings & Krainer, 2001, *Curr. Opin. Cell Biol.*, 13, 302-309). Naturally occurring trans-splicing with the involvement of a snRNP-mediated mechanism is described for an attachment SL (spliced leader) RNA to the 5' end of mRNAs in trypanosomes (Agabian, N., 1990, *Cell*, 61, 1157-1160; Luo et al., 1999, J. Biol. Chem., 274, 31947-31954) and *Caenorhabditis elegans* (Hirsh & Huang, 1990, *Mol. Biol. Rep.*, 14, 115). These small "spliced leader" RNAs consist of the 5' exon fused to sequences that can functionally substitute for U1 snRNA in mammalian snRNP-splicing extracts. Similar trans-splicing of SL RNA was also shown in the chordates. In the ascidian protochordate *Ciona intestinalis* the mRNAs of at least seven genes undergo trans-splicing with SLRNAs (Vandenberghe et al., 2001, *Genes Dev.*, 15: 294-303). Trans-splicing of mRNAs was also demonstrated for mammalian cells (Eul et al., 1995, *EMBO J.*, 14, 3226-3235; Li et al., 1999, *J. Biol. Chem.*, 274, 11060-11071; Caudevilla et al., 2001, FEBS Lett., 507, 269-279) and *Drosophila* (Dorn et al., 2001, *Proc. Natl. Acad. Sci. USA*, 98, 9724-9729). An early indication that trans-splicing may function in plant nuclear RNA maturation came from analysis of the mRNA encoding a calcium-dependent seed-specific protein kinase (SPK) from rice (Kawasaki et al., 1999, *Plant J.*, 18, 625-632). Mapping of a cDNA clone for SPK indicated that the entire cDNA was divided into two different regions, SPK-A and SPK-B, located on different rice chromosomes. There are reports by different groups which clearly demonstrate that trans-splicing can be engineered by using splicesome-mediated mechanism (Puttaraju et al., 1999, *Nature Biotech.*, 17, 246-252; Liu et al., 2001, *Nature Biotech.*, 20, 47-52).

Group I and II introns have the ability to splice themselves out of pre-mRNA. This reaction can be performed in vitro by the RNA alone. Such RNAs with catalytic activities are generally called ribozymes. In this invention, the term ribozyme is used to name catalytic RNAs capable of performing trans-splicing reactions between separate RNA molecules. Both group I and group II introns are capable of trans-splicing in artificial systems (Been et al., 1986, *Cell*, 47, 207-216; Jacquier et al., 1986, *Science*, 234, 1099-1194; Jarrell et al., 1988, *Mol. Cell Biol.* 8, 2361-2366). Trans-splicing was also found for group II introns in split genes of chloroplasts (Kohchi et al., 1988, *Nucl. Acids Res.*, 16, 10025-10036), and for a group I intron in an artificially split gene in *Escherichia coli* (Galloway-Salvo et al., 1990, *J. Mol. Biol.*, 211, 537-549). Group I introns were first discovered in *Tetrahymena thermophila* rRNA (Cech, T. R., 1990, *Annu. Rev. Biochem.*, 59, 543-568). They require a U in the target sequence immediately 5' of the cleavage site and bind 4-6 nucleotides on the 5' side of the cleavage site. There are over 75 known members of this group up to now. They were found also in fungal and plant mitochondria (Richard & Dujon, 1997, *Curr. Genet.*, 32, 175-181; Cho et al., 1998, *Proc. Natl. Acad. Sci. USA*, 95, 14244-14249), chloroplasts (Turmel et al. 1993, *J. Mol. Biol.* 232, 446-46), phage T4 (Galloway et al., 1990, J. Mol. Biol., 211, 537-549), blue-green algae, and other organisms.

There are several developed approaches and engineered ribozymes which can be used to practice this invention (references cited above). They actually cover the use of all known types of introns in order to engineer trans-splicing events in eukaryotic cell. In addition to used in this invention, ribozymes engineered on the basis of group I Tetrahymena introns (U.S. Pat. No. 6,015,794; Ayre et al., 1998, *Proc. Natl. Acad. Sci. USA*, 96, 3507-3512), spliceosome-mediated (Puttaraju et al., 1999, *Nature Biotech.*, 17, 246-252; Liu et al., 2001, *Nature Biotech.*, 20, 47-52; U.S. Pat. No. 6,083,702) or group II intron-mediated trans-splicing (Mikheeva & Jarrell, 1996, *Proc. Natl. Acad. Sci. USA*, 93, 7486-7490; U.S. Pat. No. 5,498,531) is also applicable.

One application example of trans-splicing contemplated in our invention is the formation of an RNA virus-based amplicon by trans-splicing from precursors or amplicon elements. In EXAMPLES 1 and 2 we describe the ribozyme-mediated formation of a TMV-based vector expressing GFP in plants. In the first example, ribozyme-mediated amplicon assembly places the GFP gene under the control of a subgenomic promoter. In the second example, the same strategy is used to assemble a functional GFP gene from two gene fragments. These strategies can be used to assemble and express any gene of interest from its components. This can be useful approach for engineering proteins with new features, e.g. domain swap experiments. In said examples, we used *Agrobacterium*-mediated transient expression in plant cells. Alternatively, one part of pro-amplicon can be provided in the plant cell from a transgene stably integrated into the nuclear genome, whereas the other part can be delivered transiently (*Agrobacterium*-mediated delivery, microprojectile bombardment, microinjection, etc.). Different methods may be used for the delivery of pro-amplicon vectors into plant cells such as direct introduction of said vector into the cells by the means of microprojectile bombardment, electroporation or PEG-mediated transformation of protoplasts. *Agrobacterium*-mediated plant transformation also represents an efficient way of vector delivery. Thus, DNA may be transformed into plant cells by various suitable technologies such as by a Ti-plasmid vector carried by *Agrobacterium* (U.S. Pat. No. 5,591,616; U.S. Pat. No. 4,940,838; U.S. Pat. No. 5,464,763), particle or microprojectile bombardment (U.S. Pat. No. 5,100,792; EP 00444882B1; EP 00434616B1). In principle, other plant transformation methods can also be used e.g. microinjection (WO 09209696; WO 09400583A1; EP 175966B1), electroporation (EP00564595B1; EP00290395B1; WO 08706614A1), etc. The choice of the transformation method depends on the plant species to be transformed. For example, microprojectile bombardment may be preferred for monocots transformation, while for dicots, *Agrobacterium*-mediated transformation gives generally better results. Also, both parts of said pro-amplicon can be stably integrated into the nuclear DNA of the same or different plants. Crossing said transgenic plants could bring together the interacting parts of pro-amplicon. Optionally, the expression of one or both parts of pro-amplicon can be under control of an inducible promoter. In such case, exposure to abiotic or biotic factors switching on the transcription from inducible promoter can trigger the trans-splicing events.

Existing technologies for controlling gene expression in plants are usually based on tissue-specific and inducible promoters and practically all of them suffer from a basal expression activity even when uninduced, i.e. they are "leaky". Tissue-specific promoters (U.S. Pat. No. 5,955,361; WO09828431) are a powerful tool but their use is restricted to very specific areas of applications, e.g. for producing sterile plants (WO9839462) or expressing genes of interest in seeds (WO00068388; U.S. Pat. No. 5,608,152). Inducible promoters can be divided into two categories according to their induction conditions—those induced by abiotic factors (temperature, light, chemical substances) and those that can be induced by biotic factors, for example, pathogen or pest attack. Examples of the first category are heat-inducible (U.S. Pat. No. 5,187,287) and cold-inducible (U.S. Pat. No. 5,847,102) promoters, a copper-inducible system (Mett et al., 1993, *Proc. Natl. Acad. Sci.*, 90, 4567-4571), steroid-inducible systems (Aoyama & Chua, 1997, *Plant J.*, 11, 605-612; McNellis et al., 1998, *Plant J.*, 14, 247-257; U.S. Pat. No. 6,063,985), an ethanol-inducible system (Caddick et al, 1997, *Nature Biotech.*, 16, 177-180; WO09321334), and a tetracycline-inducible system (Weinmann et al., 1994, *Plant J.*, 5, 559-569). One of the latest developments in the area of chemically inducible systems for plants is a chimeric promoter that can be switched on by glucocorticoid dexamethasone and switched off by tetracycline (Bohner et al., 1999, *Plant J.*, 19, 87-95). For a review on chemically inducible systems see: Zuo & Chua, (2000, *Current Opin. Biotechnol*, 11, 146-151). Other examples of inducible promoters are promoters, which control the expression of pathogenesis-related (PR) genes in plants. These promoters can be induced by treatment of the plant with salicylic acid, an important component of plant signaling pathways in response to pathogen attack, or other chemical compounds (benzo-1,2,3-thiadiazole or isonicotinic acid) which are capable of triggering PR gene expression (U.S. Pat. No. 5,942,662). Alternatively, translational vectors approach (DE 100 61 150.8) might allow achieving the formation of an amplicon from precursor parts in different tissues or at different stages of plant development.

There are reports of controllable transgene expression systems using viral RNA/RNA polymerase provided by viral infection (for example, see U.S. Pat. No. 6,093,554; U.S. Pat. No. 5,919,705). In these systems, a recombinant plant DNA sequence includes the nucleotide sequences from the viral genome recognized by viral RNA/RNA polymerase. One of the approaches for this invention will be the use of recombinant viral switches approach (DE 101 09 354.3) for tight and reliable control of trans-splicing mediated replicon assembly. Said approach can be an integral part of this invention, as recombinant a viral switch can serve as a provector/precursor for ribozyme-mediated amplicon assembly. However, the assembled amplicon must have a selectable advantage over the viral switch, e.g. must amplify and/or spread more efficiently than an original viral switch. For example, said switch might miss some viral genes or their parts (e.g. MP—movement protein) restricting its functionality (e.g. cell-to cell movement), but can carry heterologous transcription factor that triggers transcription of engineered ribozyme in transgenic plant. Said ribozyme will interact with said viral switch (recombinant viral RNA), thus forming through trans-splicing new more efficient amplicon acquiring cell-to-cell movement.

Usually trans-splicing mediated by engineered ribozymes is a relatively precise process and leads to the formation of functional mRNA spliced at predetermined position. However, taking into the consideration the sensitivity of our approach caused by amplification of trans-spliced molecules, any miss-splicing events may have significant impact on the quality of results and the efficiency of the system. Also, the degree of precision of trans-splicing might vary significantly among different constructs. Introduction of a cis-splicing event following the trans-splicing can help to correct any mistakes caused by trans-splicing and such a step is also contemplated in our invention (cf. EXAMPLE 2). The RNA molecule generated by trans-splicing may then contains an intron within the GFP coding sequence. Such intron can be easily and precisely eliminated in a process of standard nuclear RNA cis-splicing. Said additional step of splicing (cis-splicing), introduced in a process of amplicon assembly, may add a significant degree of freedom and flexibility to the process of engineering elements involved in trans-splicing.

Figure 2:
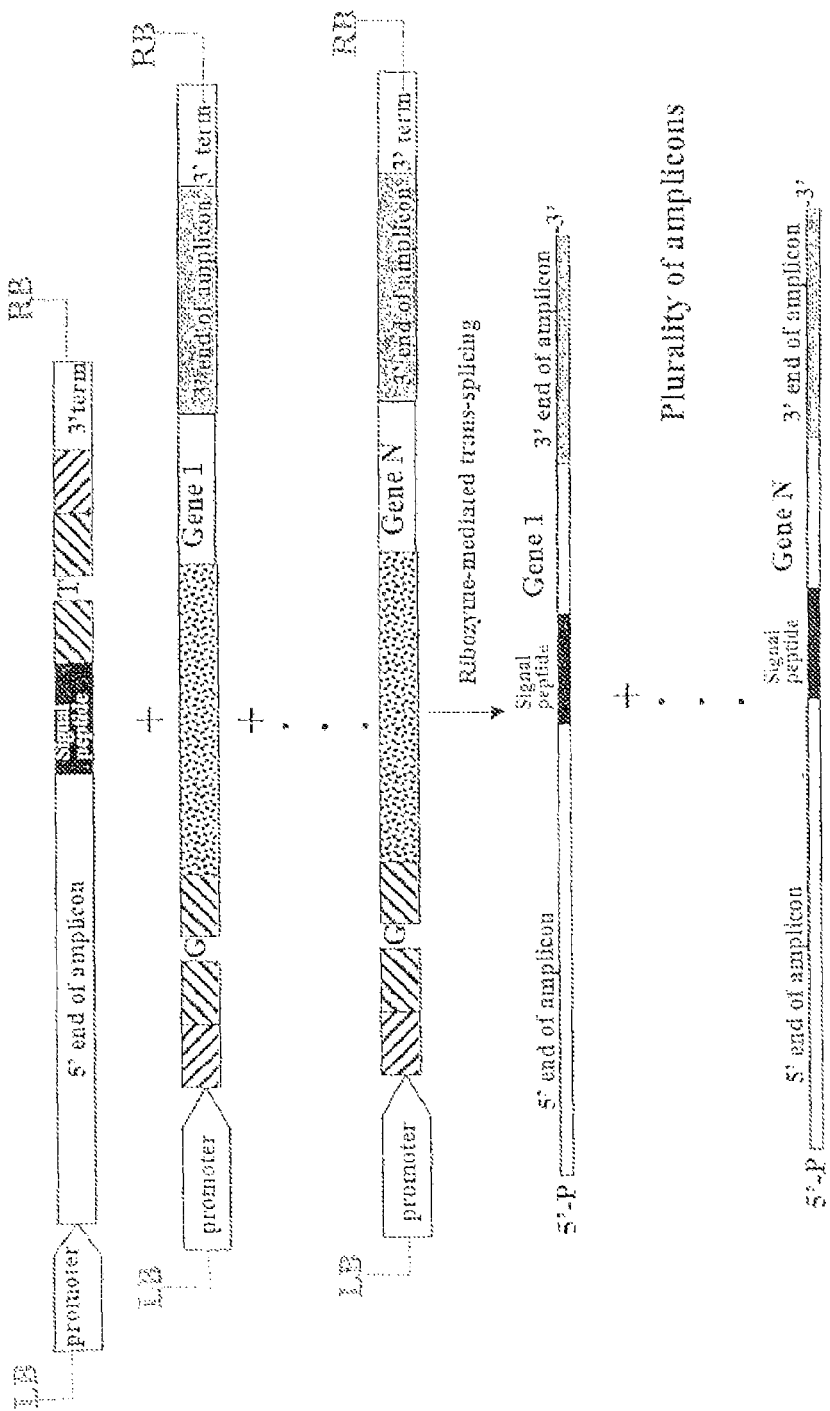
FIG. 2 General scheme, where trans-splicing fuses signal peptide with different genes of interest, thus forming a plurality of functional amplicons targeted to the same subcellular compartment.
Figure 3:
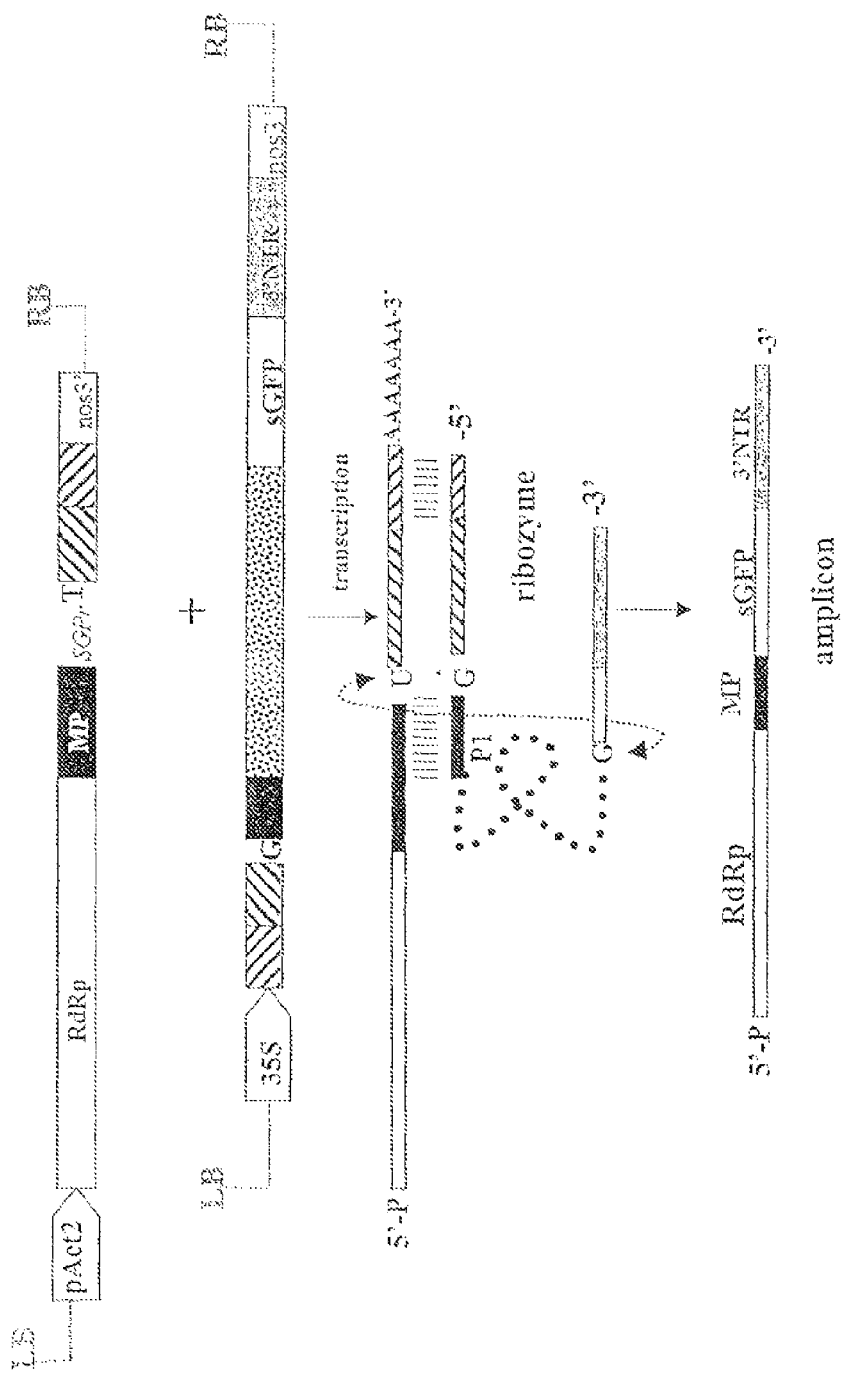
FIG. 3 Scheme, where the trans-splicing places the gene of interest (GFP) under the control of a subgenomic promoter in a tobamoviral amplicon. SGPr stands for subgenomic promoter.

Trans-splicing followed by amplification can also be used for targeting any gene(s) of interest into specific subcellular compartment. The general scheme of such experiment is shown in FIG. 2. It gives speed and efficiency necessary for delivery the same gene in many different subcellular/extracellular compartments (plastids, apoplast, mitochondria, vacuole, nucleus), or many genes in the same compartment, or both. The method of expression two different genes in the same plant cell is described in EXAMPLE 3.

The invention described here can also be used to amplify and express any mRNA present in a plant cell by using two independent trans-splicing events that specifically include any mRNA of interest into a molecule that has an amplicon property. One embodiment therefore allows rapid phenotyping of any specific resident gene of interest by selective amplification and expression of its mRNA.

The ribozyme-mediated trans-splicing followed by amplification of assembled RNA is not restricted to plant cells but it can also be used in any cell cultures/systems including animal and fungal cells. There are many vectors described which are based on yeast and animal RNA viruses and retroviruses (Agapov et al., 1998, *Proc. Natl. Acad. Sci. USA*, 95, 12989-12994; Palese, P., 1998, *Proc. Natl. Acad. Sci. USA*, 95, 12750-12752; Li et al., 2000, J. Virol., 74, 6564-6569). Additionally, many RNA viruses can be engineered in such way that they easily overcome cross-kingdom barrier. For example, animal virus FHV (flock house virus) can induce viral RNA replication, transcription, and assembly of infectious virions in transfected yeast with FHV genomic RNA yeast cells (Price, Rueckert & Alquist, 1996, *Proc. Natl. Acad. Sci. USA.*, 93, 9465-9470) and spread systemically in *N. benthamiana*, while provided with movement protein of plant viruses (Dagsupta et al., 2001, *Proc. Natl. Acad. Sci. USA.*, 98, 4910-4915). It is also very likely that many existing plant viral RNA vectors can amplify in animal or yeast cells. Moreover, it was shown that soil phytopathogen *Agrobacterium tumefaciens* can transform HeLa cells (Kunik et al., 2001, *Proc. Natl. Acad. Sci. USA*, 98, 1871-1876). This suggests that *Agrobacterium*-mediated T-DNA delivery can be used as a convenient method for introduction of plant or animal viral pro-vectors, including those for trans-splicing, into animal cells.

Interesting applications can arise from the use of retroviruses and retrotransposons. They are stably integrated into the host genomes, but can create additional copies by an RNA-mediated mechanism of transposition. The only difference between retroviruses and retrotransposons is that the latter do not have an envelope protein and, as a result, they cannot form infectious viral particles and perform cell-to-cell movement (Boeke & Corces, 1989, *Annu. Rev. Microbiol.*, 45, 403-434).

Taking into consideration the availability of RNA stage in retroviruses and retrotransposon replication, ribozyme-mediated trans-splicing can be used to form recombinant retroviral and retrotransposon-based vectors. Unlike RNA viral vectors, the assembly of functional retrovirus or retrotransposon can lead to integration event of genetically engineered retroposon into host genome. Such vectors can stably integrate into the genomic DNA of host species. The cells acquiring such integration events can be selected using selectable markers delivered through recombinant retroelement integration. This can be an addition/alternative to amplification-mediated selection for trans-splicing events (integration-mediated selection). Said approach lacks the high level of biological safety of other embodiments, as the trans-splicing product can be stably inherited in progeny, but in some cases it might offer useful solutions to problems, e.g. it might present certain interest as an alternative way of transforming eucaryotic cells. Retroviruses (U.S. Pat. No. 5,527,058; U.S. Pat. No. 6,291,740; U.S. Pat. No. 6,316,255) and retrotransposons (U.S. Pat. No. 5,354,674; U.S. Pat. No. 6,287,863; U.S. Pat. No. 6,228,647) are routinely used for yeast and animal cells transformation. However, no data were found describing the use of retrotransposons for transgene delivery into plant cells, despite that retrotransposons are widely distributed among eukaryotes including plants (Langdon et al., 2000, *Genetics*, 2000, 156, 313-325). Some of them like tobacco Tnt1 (Grandbastien et al., 1989, *Nature,* 337, 376-380; Feuerbach et al., 1997, *J. Virology,* 71, 4005-4015) and Tto1 (Hiroshika & Otsuki, 1995, *Gene,* 165, 229-232; Takeda et al., 2001, *Plant J.,* 28, 307-317) are well studied and can be used for engineering technology built on trans-splicing. Retrotransposons are activated during the stress conditions (Grandbastien, M. A., 1998, Trends Plant Sci., 3, 181-187; Takeda et al., 2001, *Plant J.,* 28, 307-317) including protoplasts isolation, tissue culture (Hiroshika et al., 1993, EMBO J., 3, 2521-2528), wounding, pathogen infection, salicylic acid treatment. Referring to the mentioned above, it becomes clear that endogenous retrotransposons can serve as targets for ribozyme-mediated trans-splicing. Modified in such way, retrotransposons can integrate into the host genome, thereby stably introducing the transgene(s) of interest. Moreover, such integrated DNA can undergo further changes by site-specific recombination in order to remove any unwanted retroposon sequences which can effect the stability of integration and transgene expression pattern (U.S. Pat. No. 6,200, 800).

To the best of our knowledge, no similar approaches were described so far. Evidently, our approach has an advantage over existing technologies, as the result of trans-splicing is amplified and, in addition, can be fixed in progeny of the targeted cell by integration of a reverse transcribed trans-splicing product.

The invention can be used to produce multiple products or longer transcripts, as it has no limitations on the insert size.

The trans-splicing system described in our invention comprises of two or more components, which can be provided in trans. This means that our system is better controlled and safer, e.g. it has zero expression level in the uninduced state.

Genes of interest, or fragments thereof, that can be expressed, in sense or antisense orientation, using this invention, include, but are not limited to: starch modifying enzymes (starch synthase, starch phosphorylation enzyme, debranching enzyme, starch branching enzyme, starch branching enzyme II, granule bound starch synthase), sucrose phosphate synthase, sucrose phosphorylase, polygalacturonase, polyfructan sucrase, ADP glucose pyrophosphorylase, cyclodextrin glycosyltransferase, fructosyl transferase, glycogen synthase, pectin esterase, aprotinin, avidin, bacterial levansucrase, *E. coli* glgA protein, MAPK4 and orthologues, nitrogen assimilation/methabolism enzyme, glutamine synthase, plant osmotin, 2S albumin, thaumatin, site-specific recombinase/integrase (FLP, Cre, R recombinase, Int, SSVI Integrase R, Integrase phiC31, or an active fragment or variant thereof), isopentenyl transferase, Sca M5 (soybean calmodulin), coleopteran type toxin or an insecticidally active fragment, ubiquitin conjugating enzyme (E2) fusion proteins, enzymes that metabolise lipids, amino acids, sugars, nucleic acids and polysaccharides, superoxide dismutase, inactive proenzyme form of a protease, plant protein toxins, traits altering fiber in fiber producing plants, Coleopteran active toxin from *Bacillus thuringiensis* (Bt2 toxin, insecticidal crystal protein (ICP), CrylC toxin, delta endotoxin, polyopeptide toxin, protoxin etc.), insect specific toxin AaIT, cellulose degrading enzymes, E1 cellulase from *Acidothermus celluloticus*, lignin modifying enzymes, cinnamoyl alcohol dehydrogenase, trehalose-6-phosphate synthase, enzymes of cytokinin metabolic pathway, HMG-CoA reductase, *E. coli* inorganic pyrophosphatase, seed storage protein, *Erwinia herbicola* lycopen synthase, ACC oxidase, pTOM36 encoded protein, phytase, ketohydrolase, acetoacetyl CoA reductase, PHB (polyhydroxybutanoate) synthase, acyl carrier protein, napin, EA9, non-higher plant phytoene synthase, pTOM5 encoded protein, ETR (ethylene receptor), plastidic pyruvate phosphate dikinase, nematode-inducible transmembrane pore protein, trait enhancing photosynthetic or plastid function of the plant cell, stilbene synthase, an enzyme capable of hydroxylating phenols, catechol dioxygenase, catechol 2,3-dioxygenase, chloromuconate cycloisomerase, anthranilate synthase, *Brassica* AGL15 protein, fructose 1,6-biphosphatase (FBPase), AMV RNA3, PVY replicase, PLRV replicase, potyvirus coat protein, CMV coat protein, TMV coat protein, luteovirus replicase, MDMV messenger RNA, mutant geminiviral replicase, *Umbellularia californica* C12:0 preferring acyl-ACP thioesterase, plant C10 or C12:0 preferring acyl-ACP thioesterase, C14:0 preferring acyl-ACP thioesterase (luxD), plant synthase factor A, plant synthase factor B, 6-desaturase, protein having an enzymatic activity in the peroxysomal-oxidation of fatty acids in plant cells, acyl-CoA oxidase, 3-ketoacyl-CoA thiolase, lipase, maize acetyl-CoA-carboxylase, 5-enolpyruvylshikimate-3-phosphate synthase (EPSP), phosphinothricin acetyl transferase (BAR, PAT), CP4 protein, ACC deaminase, ribozyme, protein having posttranslational cleavage site, protein fusion consisting of a DNA-binding domain of Gal4 transcriptional activator and a transcriptional activation domain, a translational fusion of oleosin protein with protein of interest capable of targeting the fusion protein into the lipid phase, DHPS gene conferring sulfonamide resistance, bacterial nitrilase, 2,4-D monooxygenase, acetolactate synthase or acetohydroxyacid synthase (ALS, AHAS), polygalacturonase, bacterial nitrilase, fusion of amino terminal hydrophobic region of a mature phosphate translocator protein residing in the inner envelope membrane of the plastid with protein of interest to be targeted into said membrane etc.

Any human or animal protein can be expressed using a trans-splicing system followed by amplification. Examples of such proteins of interest include inter alia immune response proteins (monoclonal antibodies, single chain antibodies, T cell receptors etc.), antigens, colony stimulating factors, relaxins, polypeptide hormones, cytokines and their receptors, interferons, growth factors and coagulation factors, enzymatically active lysosomal enzyme, fibrinolytic polypeptides, blood clotting factors, trypsinogen, 1-antitrypsin (AAT), as well as function-conservative proteins like fusions, mutant versions and synthetic derivatives of the above proteins.

The process of the invention may further comprise expressing a gene encoding a post-transcriptional gene silencing (PTGS) suppressor protein or a function-conservative variant or fragment thereof into a plant for suppressing PTGS of said transgenic coding sequence. Said PTGS suppressor protein gene or function-conservative variant or fragment thereof may be provided to a plant on the same vector carrying said transgenic coding sequence or on an extra vector. Said PTGS suppressor protein is preferably of viral or plant origin. Examples of PTGS suppressor proteins are potato virus X p25 protein, african cassaya mosaic virus AC2 protein, rice yellow mottle virus P1 protein, tomato bushy stunt virus 19K protein, rgs CAM or a function-conservative variant or fragment of one of these proteins. Said function-conservative variant or fragment preferably has a sequence identity of 75% to one of the above protein. Details on PTGS suppressor proteins and their use can be found in WO0138512.

Our invention is also applicable to selectable/scorable marker genes and their fusions with different genes of interest, thus allowing for the direct selection of the best recombinant protein producer. Examples of such selectable/scorable markers include inter alia genes or fragments of: neomycin phosphotransferase II (NPTII), hygromycin phosphotransferase, aminoglycoside 6'-N-acetyltransferase, 5-enolpyruvylshikimate-3-phosphate synthase, phosphinothricin acetyl transferase (BAR), betaine aldehyde dehydrogenase (BADH), dihydrofolate reductase (DFR1), 6' gentamicin acetyltransferase (6' GAT), acetolactate synthase (ALS), phosphomannose-isomerase (PMI), glyphosate oxidoreductase, acetohydroxyacid synthase (AHAS), 2-deoxyglucose-6-phosphate phosphatase (2-DOG-6-P), luciferase, green fluorescent protein (GFP), and selectable and screenable marker genes fusions.

Moreover, subject to further development of trans-splicing technology, this invention can be useful for differential amplification of specific host messenger RNAs.

EXAMPLE 1

Trans-Splicing-Mediated Gene Placement Under Control of Subgenomic Promoter

Two constructs carrying the 5' and 3' ends of TMV amplicon were designed using standard molecular biology techniques (Sambrook, Fritsch & Maniatis, 1989, *Molecular Cloning: A Laboratory Manual*, Cold Spring Harbor Lab Press, Plainview, N.Y., $2^{nd}$ edition). The first construct (FIG. 3, top) carries the 5' end of a TMV amplicon containing the RdRp (RNR-dependent RNA polymerase) gene, the MP (movement protein) gene and the CP (coat protein) subgenomic promoter (SGPr) followed by sequences complementary to the variable part of artificial ribozyme (see FIGS. 3 and 7). The second construct additionally contains a full length sGFP gene and 3'NTR (non-translated region) of TMV. Schematic presentations of the constructs as well as the products of their trans-splicing are shown in FIGS. 3 (general scheme) and 7 (in detail).

Cloning of the 5'-End of the Trans-Splicing System

A part of the HPT gene (300 nucleotides, the sequence is shown below) was chosen as the target sequence. HPT is a bacterial gene, it is not related to any of the plant genes. The G/C content is about 60%, so base pairing between 5' and 3' parts of the viral vector should be quite efficient:

```
attgctgatcccatgtgtatcactggcaaactgtgatggacgacaccgt
cagtgcgtccgtcgcgcaggctctcgatgagctgatgctttgggccgagg
actgccccgaagtccggcacctcgtgcacgcggatttcggctccaacaat
gtcctgacggacaatggccgcataacagcggtcattgactggagcgaggc
gatgttcggggattcccaatacgaggtcgccaacatcctcttctggaggc
cgtggttggcttgtatggagcagcagacgcgctacttcgagcggaggcat
```

The following primers were ordered for the amplification of the HPT-target sequence: (restriction sites are written in bold letters and underlined):

```
Targhpt1:
5'-atgcctcgagttactagaattgctgatcccatgtgtatcac-3'
        XhoI

Targhp2:
5'-tcagggatccatgcctccgctcgaagtagcgcgt-3'
        BamHI

Targhpt4:
5'-tgactctagaattgctgatcccatgtgtatcac-3'
        XbaI

Targhpt5:
5'-tcagagatctatgcctccgctcgaagtagcgcgt-3'
        BglII
```

Construct pICH1600 was taken as template and these oligonucleotides were used for PCR amplification of the target sequence. PCR products 1 (obtained with primers targhpt1 and targhpt5) and 2 (primers targhpt4 and targhpt5) were cloned into the pGEM-T vector (Promega) to obtain plasmids pICH7668 and pICH7685, respectively. PCR product 1 was also digested with XhoI and BglII and cloned into pICH6549 between XhoI and BamHI sites to obtain intermediate construct pICH7784 (HPT-target fused to the nos terminator).

Figure 7:
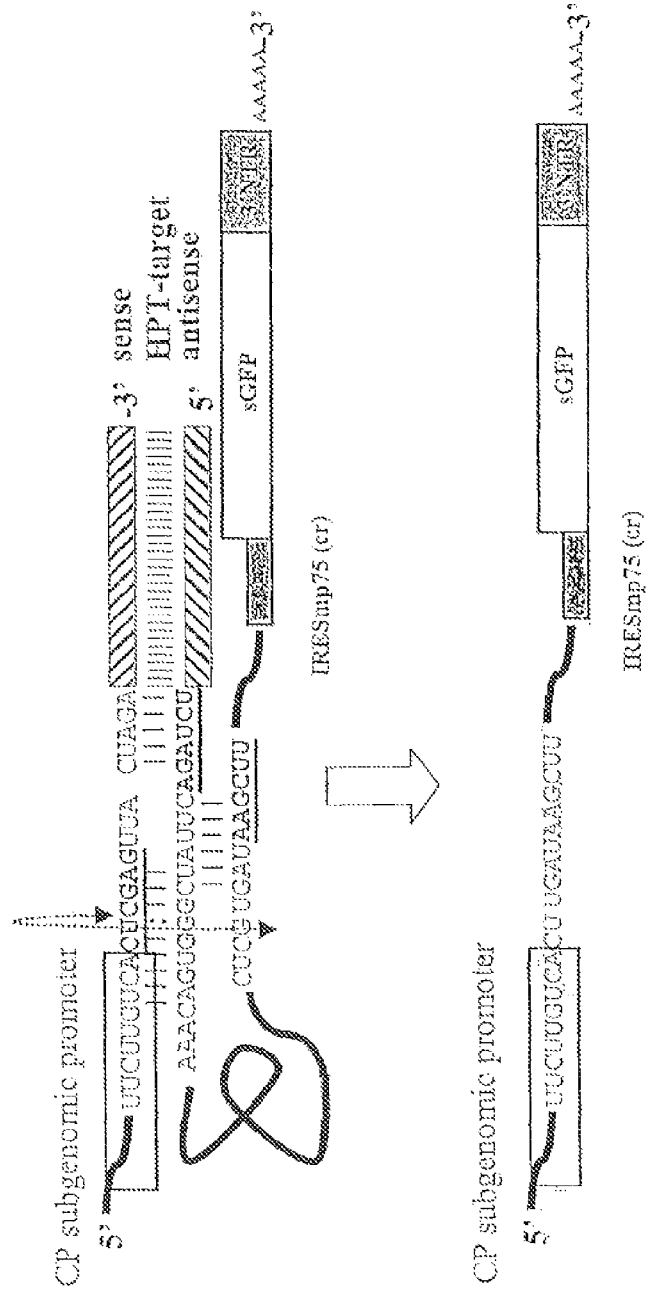
FIG. 7 Detailed mechanism of trans-splicing leading to amplicon formation.
Figure 8:
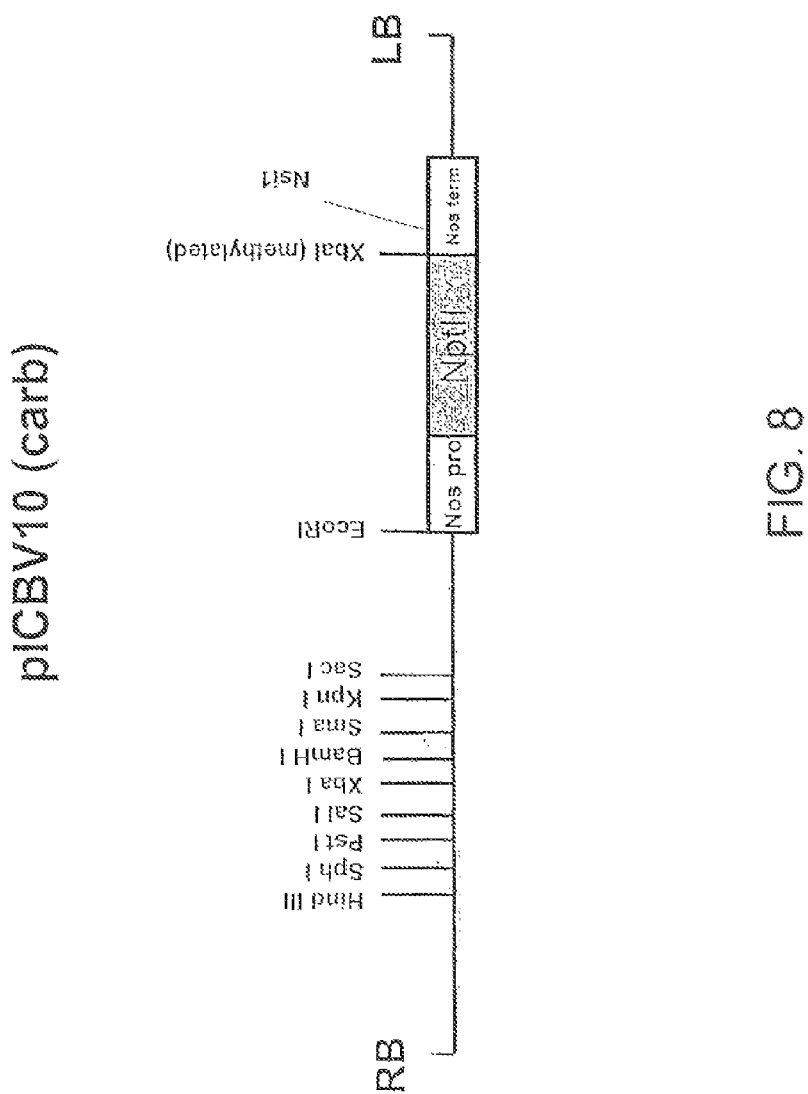
FIG. 8 depicts plasmid pICBV10 (carb).

Another intermediate plasmid was cloned for the 5' part of the trans-splicing system—it was necessary to optimize the context of the MP stop codon for the optimal basepairing and splicing (see FIG. 7). For that purpose, two other primers were used in PCR amplification of the template pICH3461:

```
Targmod1(p):
5'-tgtggttgacgaattcgtcgattcggttgcagca-3'
             EcoRI

Targmod2(m):
5'-agtcctcgagtgacaattattcgggtttgtaatgttgtaa-3'
        XhoI
```

Figure 12:
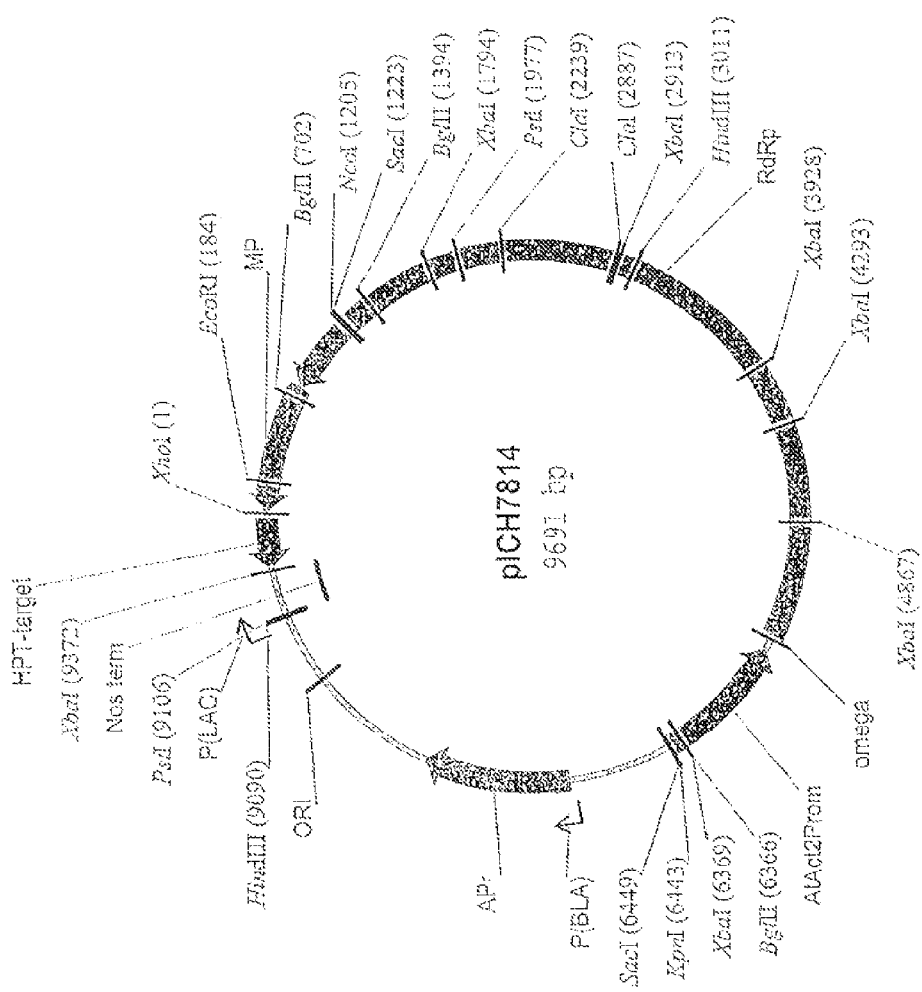
FIG. 12 depicts plasmid pICH7814.

Then, the PCR product was cloned into pGEM-T (pICH7671), cut out and inserted into pICH3461 between EcoRI and XhoI restriction sites (pICH7765). The final construct pICH7814 (Act2Promoter-RdRp-MP-HPT/target (sense)-nos terminator, cf. FIG. 12) was obtained from pICH7765 (vector, XhoI/BamHI sites) and pICH7668 (insert, XhoI/BglII).

Figure 14:
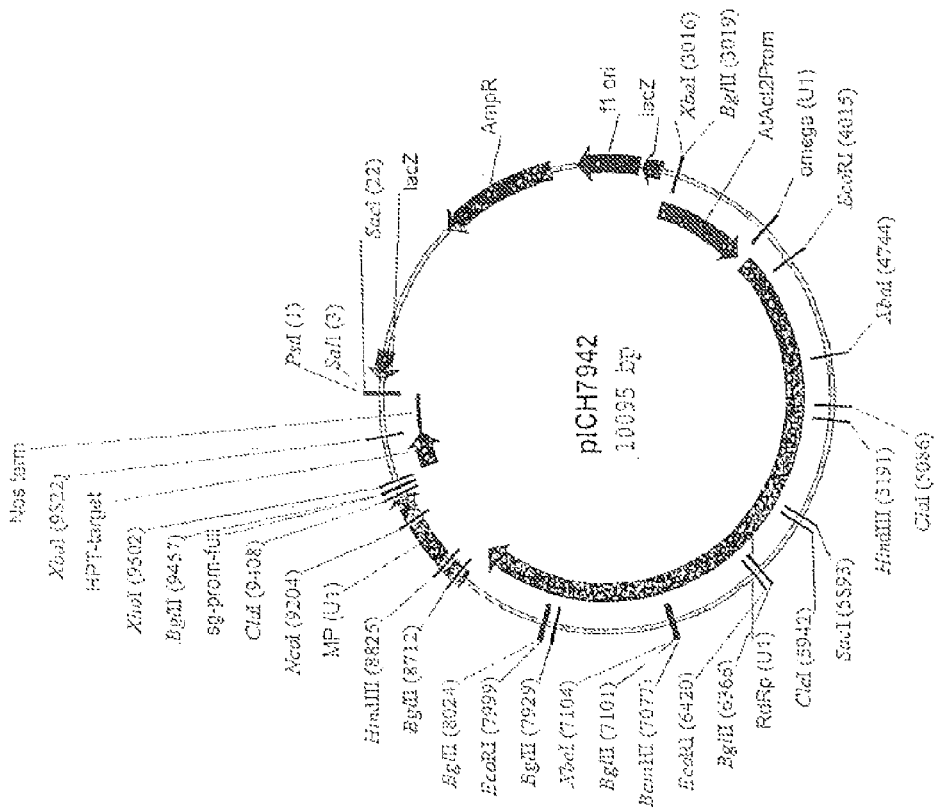
FIG. 14 depicts plasmid pICH7942.

TMV-U1-based version of the 5'-part of the trans-splicing system (pICH7942, cf. FIG. 14) was constructed from pICH7937 (Act2Promoter-RdRp(U1)-MP(U1)-full version of CP subgenomic promoter-XhoI-CP-3'NTR-nos terminator) and pICH7784 by placing HPT/target (sense)-nos terminator between XhoI and PstI restriction sites instead of CP-3'NTR-nos terminator.

Both pICH7814 and pICH7942 were tested (together with 7752 and 7950, respectively; see below) by particle bombardment of Nicotiana benthamiana leaves. For agroinfiltration experiments, they were cloned into pBin19 either between KpnI/HindIII (pICH7814) or Kpn/SalI (pICH7942) restriction sites.

Cloning of the 3'-End of the Trans-Splicing System

A sequence of synthetic ribozyme based on group I intron was taken from *Tetrahymena thermophila* precursor 26S rRNA (Koehler et al., 1999, J. Mol. Biol., 285, 1935-1950; Ayre et al., 1999, Proc. Natl. Acad. Sci. USA, 96, 3507-3512).

```
XbaI
tctagacttatcgggtgacaaaagttatcaggcatgcacctggtagctag
tctttaaaccaatagattgcatcggtttaaaaggcaagaccgtcaaattg
cgggaaaggggtcaacagccgttcagtaccaagtctcaggggaaactttg
agatggccttgcaaagggtatggtaataagctgacggacatggtcctaac
cacgcagccaagtcctaagtcaacagatcttctgttgatatggatgcagt
tcacagactaaatgtcggtcggggaagatgtattcttctcataagatata
gtcggacctctccttaatgggagctagcggatgaagtgatgcaacactgg
agccgctgggaactaatttgtatgcgaaagtatattgattagttttggag
tactcgtgataagctt
        HindIII
```

Figure 9:
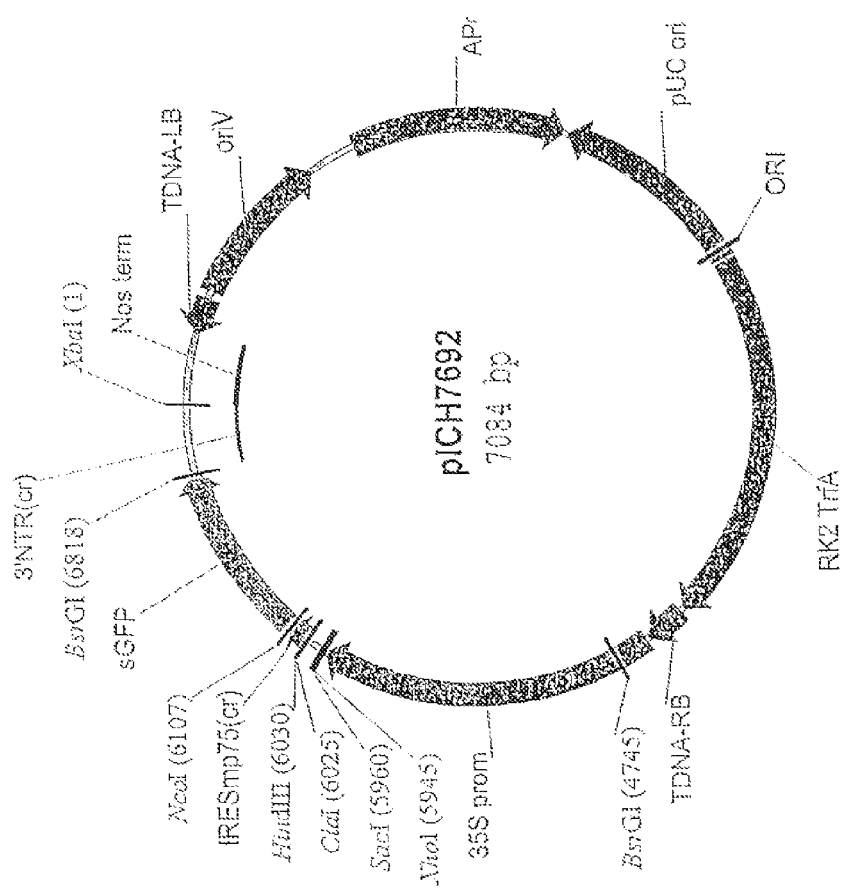
FIG. 9 depicts plasmid pICH7962.
Figure 10:
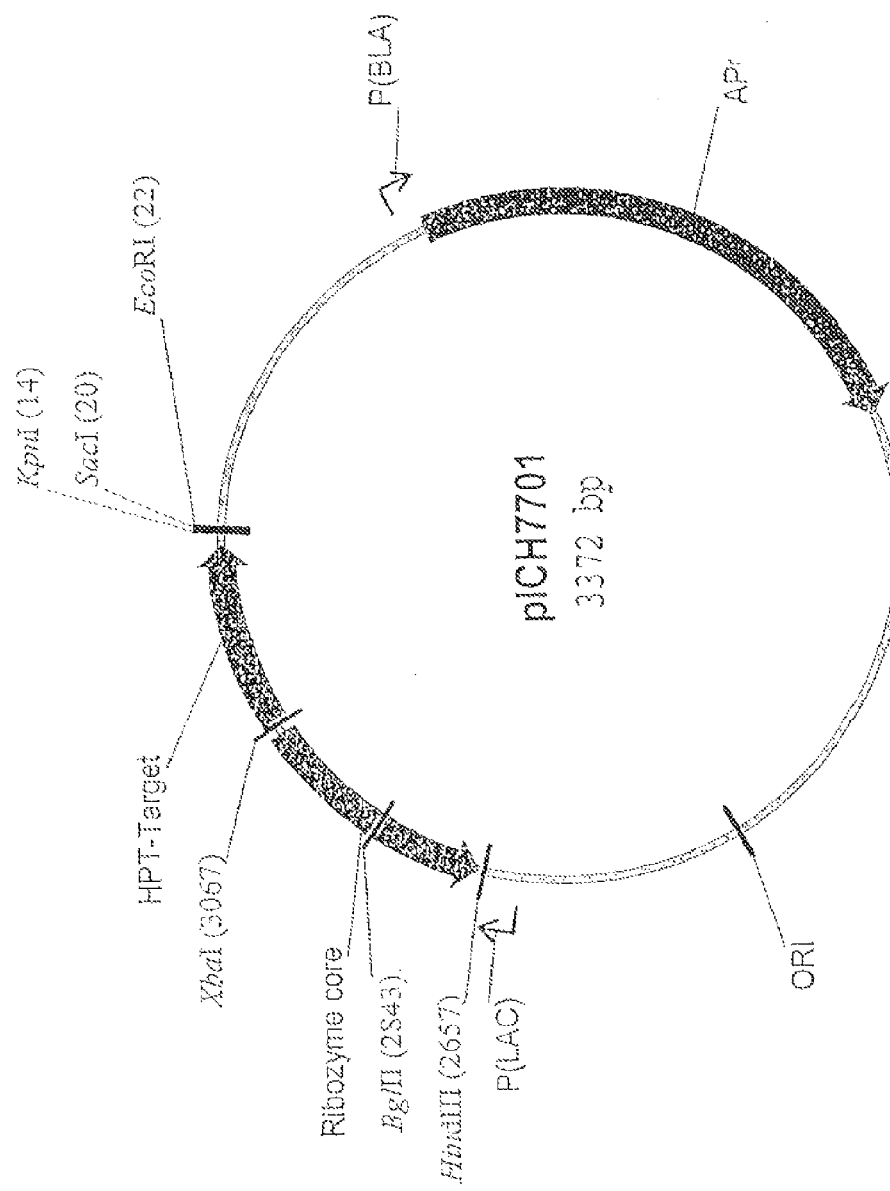
FIG. 10 depicts plasmid pICH7701.
Figure 11:
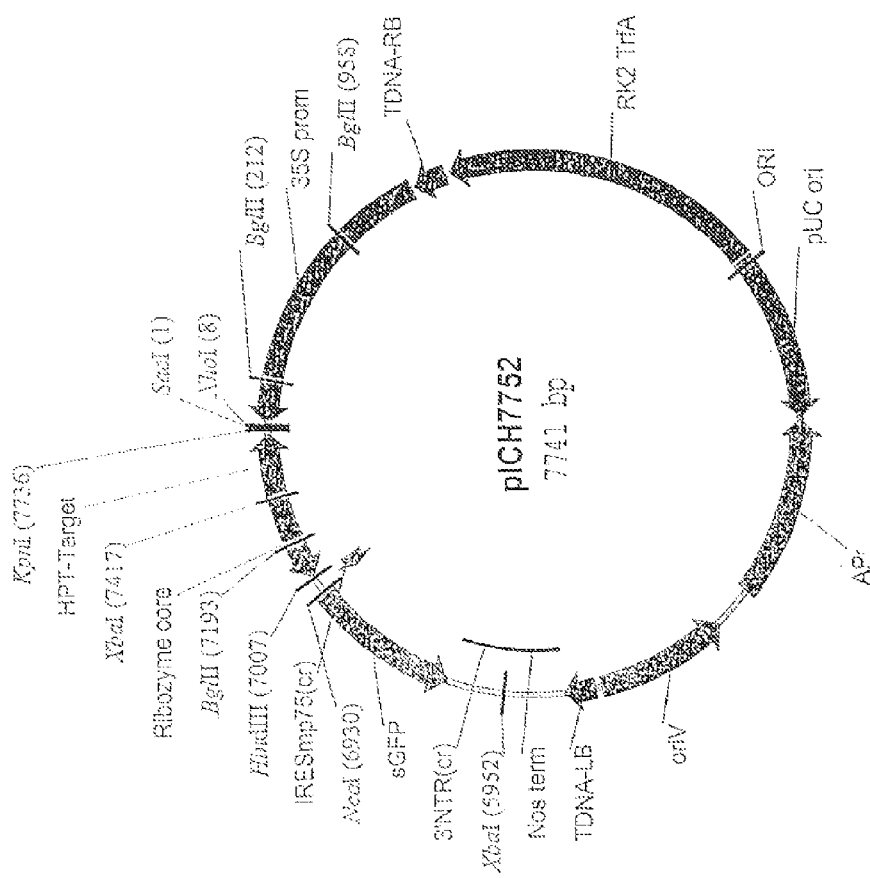
FIG. 11 depicts plasmid pICH7752.

This ribozyme sequence was ordered at ATG:Biosynthetics GmbH (P0202001), inserted into pBluescript II SK(+) between HindIII and XbaI restriction sites (plasmid pICH080) and used for further cloning steps. Then, ribozyme from pIC080 (HindIII/XbaI) was fused to the antisense version of the HPT-target (pICH7684, XbaI/BglII) to get the primary plasmid pICH7701 (pUC19 as a vector, HindIII/BamHI; FIG. 10). Intermediate construct pICH7692 (RB-35S Promoter-IRESmp75 (cr) (as translational enhancer)-sGFP-3'NTR-nos-LB; FIG. 9) was obtained in two-fragment cloning from binary vector pICBV14 (digested with ClaI/XbaI) and two inserts: pICH1731 (ClaI/BsrGI) and pICH5332 (BsrGI/XbaI). During the last step of cloning both pICH7701 and pICH7692 were used to obtain the final 3'-part of the trans-splicing vector pICH7752 (RB-35S Promoter-HPT/target (antisense; FIG. 11)-ribozyme-IRESmp75(cr) (as translational enhancer)-sGFP-3'NTR-nos-LB).

Figure 13:
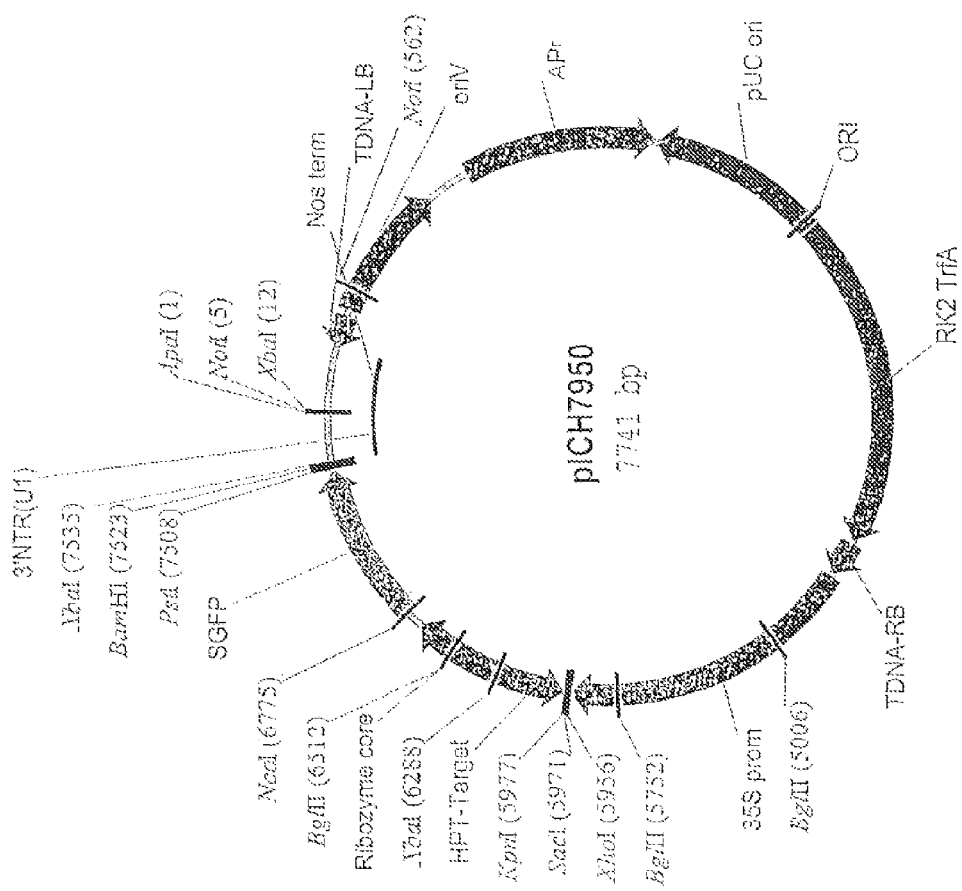
FIG. 13 depicts plasmid pICH7955.

To get TMV-U1-based version of the 3'-part of the trans-splicing system (pICH7955; FIG. 13) plasmid pICH7752 was digested by NcoI/ApaI and ligated with NcoI/ApaI fragment (sGFP-3'NTR(U1)) from pICH6671.

Constructs pICH7752 and pICH7955 were tested by either particle bombardment (see below) or agroinfiltration (Vaquero et al., 1999, *Proc. Natl. Acad. Sci. USA*, 96, 11128-11133) of *Nicotiana benthamiana* and GFP fluorescence was detected with UV lamp (385 nm).

Microprojectile Bombardment

Microprojectile bombardment was performed utilizing the Biolistic PDS-1000/He Particle Delivery System (Bio-Rad). Separate *N. benthamiana* leaves were bombarded at 1100 psi, with 15 mm distance from a macrocarrier launch point to the stopping screen and 60 mm distance from the stopping screen to a target tissue. The distance between the rupture disk and a launch point of the macrocarrier was 12 mm.

The DNA-gold coating procedure (PEG/Mg) was performed as follows: 50 μl of gold suspension (60 mg/ml in 50% glycerol) was mixed with 5-10 μl of plasmid DNA (up to 1 μg/μl) in an siliconized eppendorf tube and supplemented subsequently by 15 μl of 40% PEG in 1.0 M $MgCl_2$. The mixture was vortexed for 2 min and than incubated for 30 min on ice. After centrifugation (2000 rpm, 1 min) the pellet was dispersed finally in 30 μl of absolute ethanol. Aliquots (6 μl) of DNA-gold suspension in ethanol were loaded onto macrocarrier disks and allowed to dry up for 5-10 min.

EXAMPLE 2

Trans-Splicing-Mediated Assembly of a Full Length Coding Sequence

Figure 4:
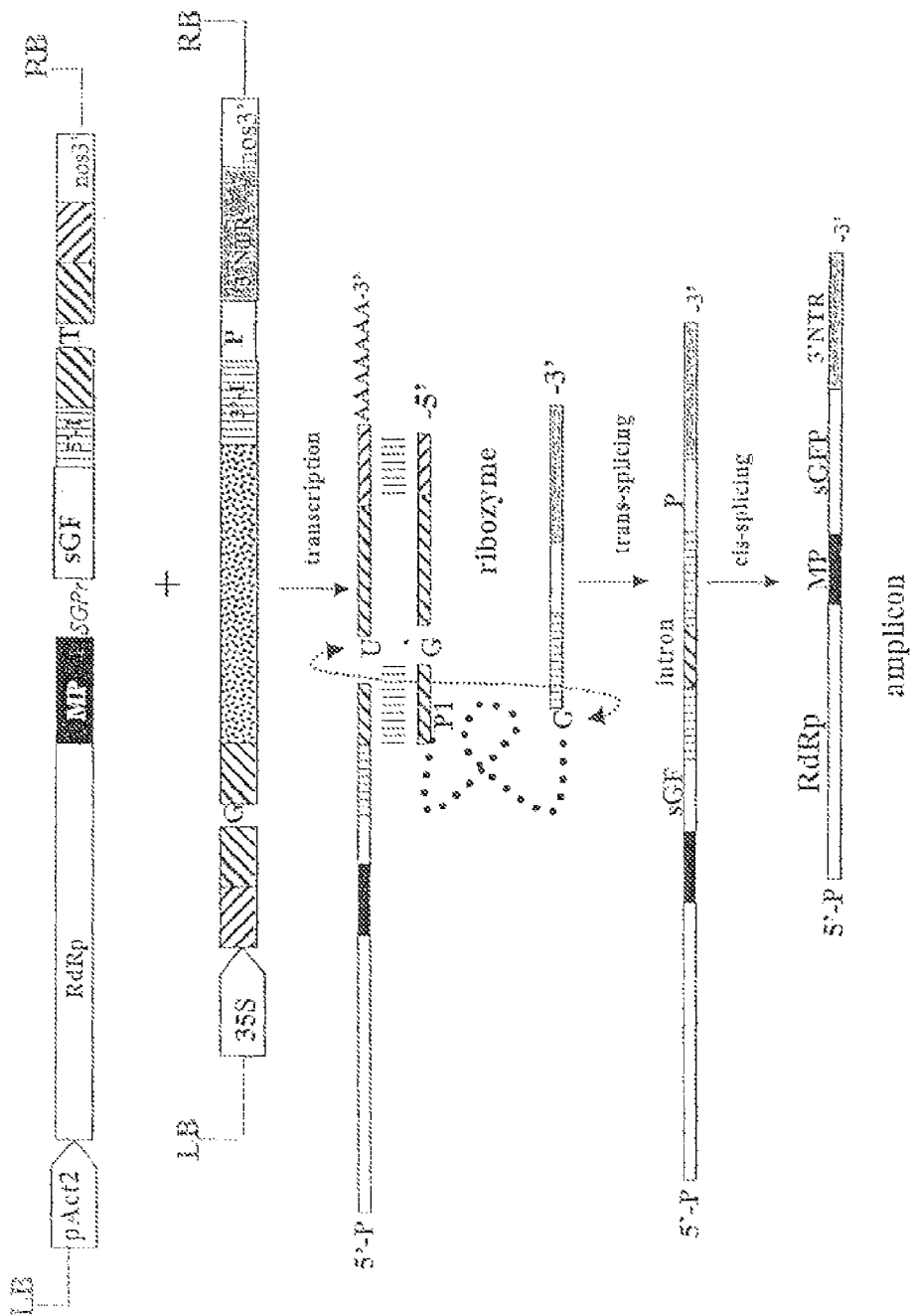
FIG. 4 Scheme, where trans-splicing and cis-splicing leads to the assembly of a functional gene of interest (GFP) in tobamovirus-based amplicon. sGF stands for the N-terminal part of a synthetic GFP. P stands for the C-terminal part of said GFP. MP stands for movement protein.

Two constructs were designed using an approach described in EXAMPLE 1. Schematic representations of the constructs as well as the product of trans-splicing are shown in FIG. 4. The difference to example 1 is that in addition to a subgenomic promoter, the 5' end of the pro-amplicon contains the 5' end of GFP (sGF) (optionally with the 5' end of the *Arabidopsis* Actin2 intron 1) followed by sequences recognizable by the synthetic ribozyme and a transcription termination signal. The 3' end of pro-amplicon consists of a synthetic ribozyme designed as described by Ayre et al. (1999, *Proc. Natl. Aced. Sci. USA*, 96, 3507-3512), except that the 3' end of the ribozyme consists of 3' end of GFP (optionally preceded by 3' end of ADH1 intron), followed by TMV 3' non-translated region (3'NTR) and eukaryotic transcription termination region. Both constructs were placed under the control of the *Arabidopsis* Actin 2 promoter and recloned into binary vector of pICBV family (see FIG. 7). The experiments were carried out using *Agrobacterium*-mediated transient expression (Vaquero et al., 1999, *Proc. Natl. Acad. Sci. USA*, 96, 11128-11133) of both constructs together in *N. benthamiana* leaves. The ribozyme-mediated trans-splicing of transcripts from these constructs led to the formation of functional TMV amplicon expressing GFP protein. The sGFP presence was easily detectable under UV light in infiltrated area of *N. benthamiana* leaves.

EXAMPLE 3

Figure 5:
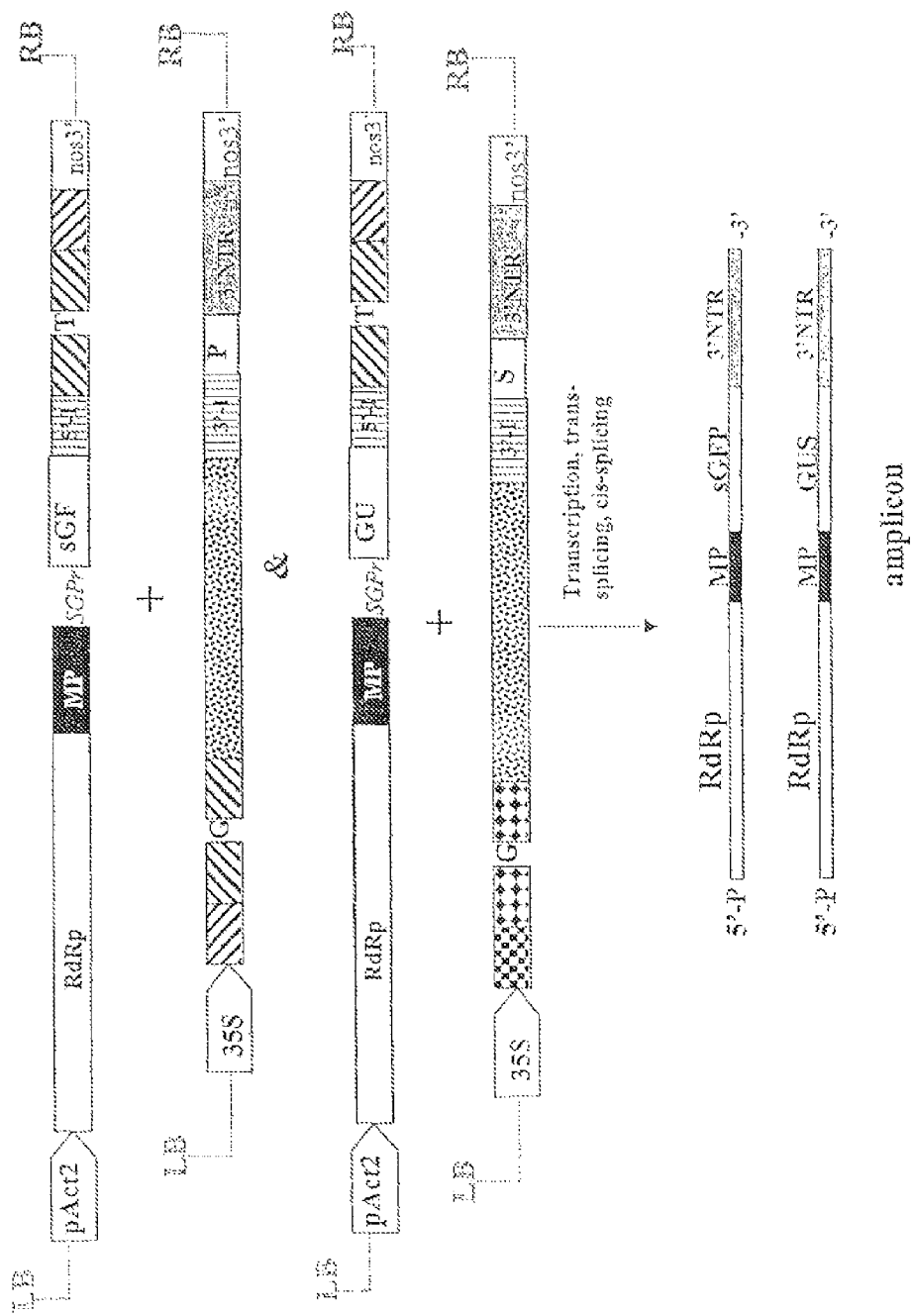
FIG. 5 Scheme, where trans-splicing leads to the formation of two amplicons with different transgenes. GU stands for an N-terminal part of GUS. S stands for a C-terminal part of GUS. RdRp stands for RNA dependent RNA polymerase.

Use of Trans-Splicing for Expression of more than One Gene in the Same Plant Cell Two additional constructs which are similar to those described in EXAMPLE 2, but which carry two parts of the GUS gene (indicated by GU and S in FIG. 5) were obtained from pICH7942 and 7955 and placed into the binary vectors (pICBV family or pBin19, see Examples 1 and 2). The *Agrobacterium* strains carrying pro-amplicons with the two parts of GUS were mixed together with the *Agrobacterium* strains carrying two parts of GFP pro-amplicon and inoculated into leaves of growing *N. benthamiana* plants. The plants were monitored for GFP expression with the help of a UV lamp one week after the inoculation. Leaves expressing GFP were used for the detection of GUS activity by staining with x-gluc (Jefferson, Kavanagh & Bevan, 1987, *EMBO J.*, 6, 3901-3907). The blue-stained sectors of the GUS activity co-localized with the sectors of GFP activity in most of the inoculated leaf tissues. A schematic representation of this experiment is shown in FIG. 5.

EXAMPLE 4

Figure 6:
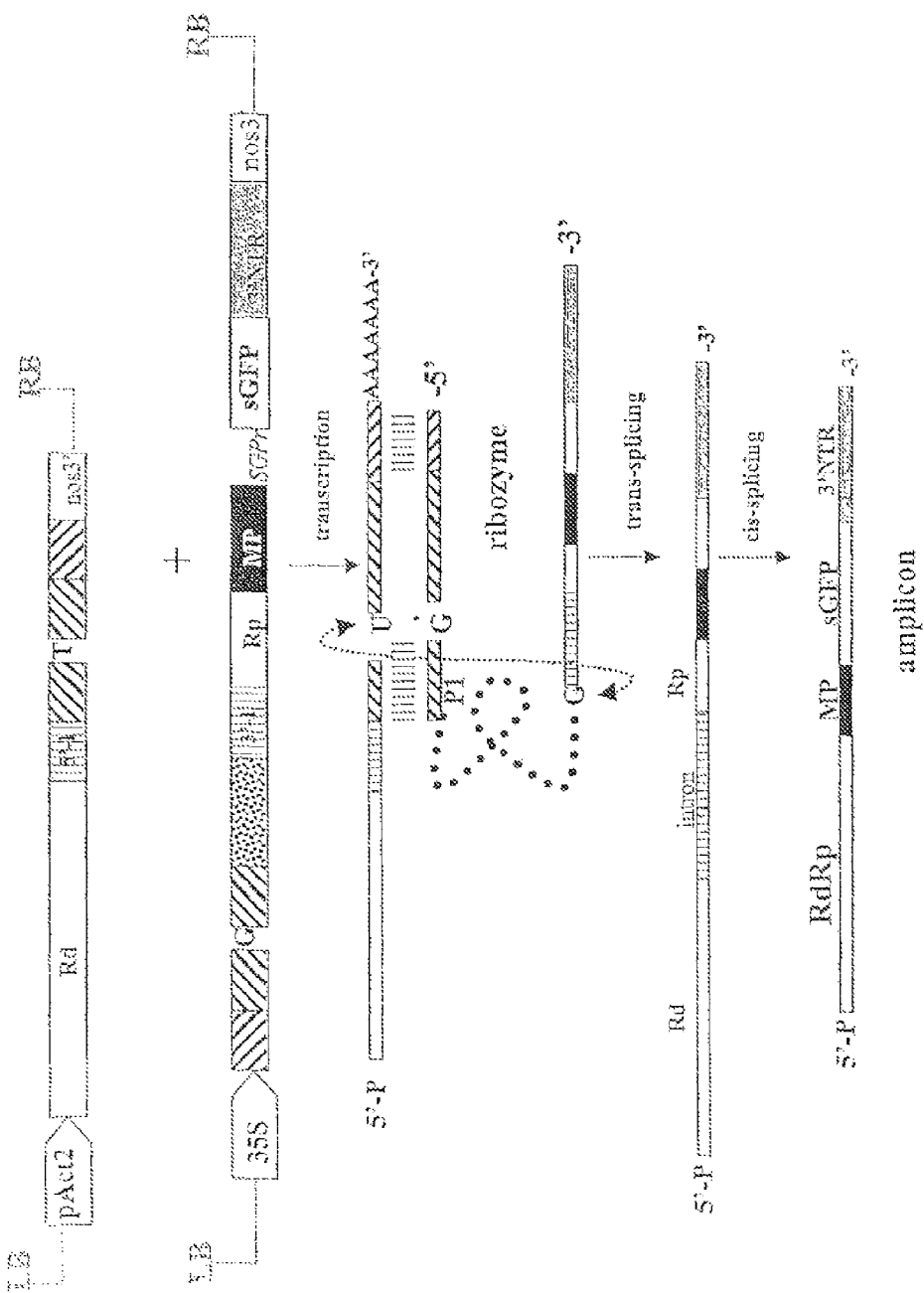
FIG. 6 Scheme, where the trans-splicing leads to the assembly of functional viral gene (RdRp) in tobamovirus-based amplicon. Rd and Rp stand for the N- and C-terminal parts, respectively, of RdRp.

Assembly of Functional Viral Gene(s) Via Trans-Splicing Leads to Amplicon Capable of Amplification and Cell-to Cell Movement More constructs were designed from the basic plasmids described in EXAMPLE 1. Schematic representation of these constructs together with the product of their trans-splicing is given in FIG. 6. The 5' end of the trans-splicing system (modified from pICH7963) contains the *Arabidopsis* Actin 2 promoter, the N-terminal part of the TMV-U1 replicase gene (N-terminal part of RdRp designated Rd in FIG. 6) from the start codon to BamHI site with 5' end of *Arabidopsis* Actin2 intron 1 followed by HPT-target in sense orientation (see Example 1) and nos termination/polyA addition signal. The 3' end of the system was obtained from primary constructs pICH6549 and pICH7652 and consists of 35S promoter, HPT-target (antisense orientation) fused to the synthetic ribozyme (taken from pICH7752, see above), 3' end of ADH1 intron, C-terminal part of RdRp gene (designated Rp in FIG. 6) followed by MP gene, sGFP gene under control of CP subgenomic promoter, TMV 3' non-translated region (3'NTR) and nos termination/polyA addition signal.

The experiment was performed using particle bombardment (see Example 1). Like in Examples 1 and 2, GFP was expressed in *N. benthamiana* leaves, but this time, instead of reporter gene of interest (GFP or GUS), the functional viral gene (RdRp) was restored, leading to efficient replication and cell-to-cell movement.

The invention claimed is:

1. A process of amplification and/or expression of a sequence of interest in a plant cell said process comprising:
providing a plant cell with an RNA sequence comprising a ribozyme; and
generating within said cell at least one plant RNA viral amplicon by trans-splicing between said RNA sequence and a target RNA, wherein said RNA sequence is designed for catalyzing said trans-splicing, whereby said amplicon is capable of amplifying in said cell and capable of expressing a sequence of interest, and wherein said cell is provided with an RNA-dependent RNA polymerase for enabling amplification of said amplicon.

2. The process according to claim 1, wherein said process comprises directly providing said cell with said RNA sequence.

3. The process according to claim 1, wherein said providing said cell with said RNA sequence comprises providing said cell with a DNA sequence capable of being transcribed in said cell to produce said RNA sequence.

4. The process according to claim 2, wherein said providing said cell with said RNA sequence comprises providing said RNA sequence by viral transfection, *Agrobacterium*-mediated delivery, non-biological delivery, or by conversion of a precursor DNA that was pre-integrated into a nuclear DNA or was maintained in the nucleus autonomously to form an RNA sequence designed for catalyzing said trans-splicing with a target RNA.

5. The process according to claim 1, wherein said RNA sequence further contains a sequence of interest.

6. The process according to claim 5, wherein said sequence of interest comprises portions having self-complementarity for forming a double-stranded RNA structure.

7. The process according to claim 1, wherein said target RNA is an endogenous RNA of said cell.

8. The process according to claim 1, wherein said cell is provided with said target RNA by viral transfection, *Agrobacterium*-mediated delivery, non-biological delivery, or by conversion of a precursor DNA that was pre-integrated into a nuclear DNA or was maintained in the nucleus autonomously to form an RNA sequence designed for being capable of trans-splicing with a target RNA.

9. The process according to claim 1, wherein said amplicon is of RNA virus origin.

10. The process according to claim 1, wherein said cell is provided with two or more RNA sequences designed for catalyzing said trans-splicing.

11. The process according to claim 1, wherein said trans-splicing produces two or more amplicons.

12. The process according to claim 1, wherein said trans-splicing is followed by cis-splicing of said RNA amplicon generated from said trans-splicing.

13. The process according to claim 1, wherein one of said amplicons is a fully functional autonomous amplicon that is capable of amplification in said cell and that provides in trans functions necessary for replication of other non-autonomous amplicon(s).

14. The process according to claim 1, wherein one of said amplicons is a wild type virus or an attenuated wild type virus which provides in trans one or more functions necessary for replication of other amplicon(s).

15. The process according to claim 1, wherein one or more of said amplicons retain viral or retrotransposon functions selected from the group consisting of infectivity, ability to assemble viral particles, cell to cell movement, reverse transcription, integration into a host chromosome and systemic movement.

16. The process according to claim 1, wherein said cell is of wild type.

17. The process according to claim 1, wherein said trans-splicing assembles an RNA sequence of interest or a transcription unit, whereby said RNA sequence and said target RNA each provide a part of said sequence of interest or of said transcription unit.

18. The process according to claim 17, wherein said trans-splicing assembles in a transcription unit genetic elements selected from the following group: transcriptional and translational signals or elements; introns, exons, inteins or exteins; signal, transit, targeting or attachment motifs; purification and visualization tags; catalytic, recognition, affinity or other functional domains or parts thereof, whereby said genetic elements are derived from one or more genes or are engineered artificially.

19. The process according to claim 17, which is used for directed evolution of a gene or of a gene control element.

20. The process according to claim 1, wherein said process results in amplification and/or expression of more than one sequence of interest, necessary for simultaneous production of polypeptides required for multimer protein production.

21. The process according to claim 20, wherein said multimer protein is an immune response protein such as human or animal monoclonal antibody.

22. The process according to claim 1, wherein said process results in amplification and/or expression of sequences of interest for the purpose of functional genomics, gene identification, gene function determination, biochemical pathway analysis or selective screening.

23. The process according to claim 1, wherein said process results in specific amplification and/or expression of nucleic acid sequences for the purpose of biochemical production or therapy.

24. The process according to claim 1, wherein said RNA sequence designed for catalyzing said trans-splicing is selected from the following group: group I introns, group II introns, genetically altered or artificial introns, or pro-introns which upon processing by a host cell generate a ribozyme capable of specific trans-splicing.

25. The process according to claim 1, wherein a biochemical process or biochemical cascade of interest is switched on by said trans-splicing and/or said amplification.

26. Cells, tissues, or an organism excluding humans or material thereof, said cells, tissues, or organism obtained by performing the process according to claim 1, wherein said sequence of interest is heterologous to said cell.

27. A vector for performing the process according to claim 1, said vector having or coding for an RNA sequence catalyzing said trans-splicing with a target RNA.

28. A kit-of-parts comprising (i) plant cells, plant seeds or plants, or animal cells or animals excluding humans, and (ii) vectors according to claim 27.

29. The process according to claim 7, wherein said endogenous RNA is a messenger RNA.

30. The process according to claim 1, wherein said RNA amplicon encodes said RNA-dependent RNA polymerase.

31. A process of amplification and/or expression of a sequence of interest in a cell, said process comprising:
providing a cell with an RNA sequence; and
generating within said cell at least one RNA amplicon by trans-splicing between said RNA sequence and a target RNA, wherein said RNA sequence is designed for catalyzing said trans-splicing, and whereby said amplicon is capable of amplifying in said cell and capable of expressing a sequence of interest, and wherein said RNA amplicon contains a plant RNA viral origin of replication.

32. A process of amplification and/or expression of a sequence of interest in a cell, said process comprising:
providing a cell with an RNA sequence; and
generating within said cell at least one RNA amplicon by trans-splicing between said RNA sequence and a target RNA, wherein said RNA sequence is designed for catalyzing said trans-splicing, and whereby said amplicon is capable of amplifying in said cell and capable of expressing a sequence of interest, and wherein said cell is a plant cell.

* * * * *